US009743978B2

(12) United States Patent
Skalyni

(10) Patent No.: US 9,743,978 B2
(45) Date of Patent: Aug. 29, 2017

(54) SYSTEMS AND METHODS FOR ENDOMETRIAL ABLATION

(71) Applicant: Minerva Surgical, Inc., Cupertino, CA (US)

(72) Inventor: Eugene Skalyni, Hillsborough, CA (US)

(73) Assignee: Minerva Surgical, Inc., Cupertino, CA (US)

( * ) Notice: Subject to any disclaimer, the term of this patent is extended or adjusted under 35 U.S.C. 154(b) by 327 days.

(21) Appl. No.: 13/685,951

(22) Filed: Nov. 27, 2012

(65) Prior Publication Data

US 2013/0206147 A1    Aug. 15, 2013

Related U.S. Application Data

(60) Provisional application No. 61/570,144, filed on Dec. 13, 2011.

(51) Int. Cl.
| | | |
|---|---|---|
| *A61F 6/16* | (2006.01) | |
| *A61B 18/14* | (2006.01) | |
| *A61F 6/14* | (2006.01) | |
| *A61B 18/04* | (2006.01) | |
| *A61B 18/00* | (2006.01) | |

(52) U.S. Cl.
CPC ........ *A61B 18/1485* (2013.01); *A61B 18/042* (2013.01); *A61F 6/146* (2013.01); *A61F 6/16* (2013.01); *A61B 2018/0022* (2013.01); *A61B 2018/00559* (2013.01); *A61B 2018/00577* (2013.01)

(58) Field of Classification Search
USPC ............... 128/830–842; 424/430; 606/41
See application file for complete search history.

(56) References Cited

U.S. PATENT DOCUMENTS

| | | | |
|---|---|---|---|
| 4,611,604 A | 9/1986 | Botvidsson et al. | |
| 4,979,948 A | 12/1990 | Geddes et al. | |
| 5,191,883 A | 3/1993 | Lennox et al. | |
| 5,372,584 A * | 12/1994 | Zink ................ | A61B 10/0291 604/178 |
| 5,540,658 A | 7/1996 | Evans et al. | |
| 5,549,546 A * | 8/1996 | Schneider .......... | A61M 13/003 604/23 |
| 5,653,692 A | 8/1997 | Masterson et al. | |
| 5,769,880 A | 6/1998 | Truckai et al. | |
| 5,891,134 A | 4/1999 | Goble et al. | |
| 5,925,038 A | 7/1999 | Panescu et al. | |
| 6,041,260 A | 3/2000 | Stern et al. | |
| 6,296,639 B1 | 10/2001 | Truckai et al. | |
| 6,663,626 B2 | 12/2003 | Truckai et al. | |
| 6,736,811 B2 | 5/2004 | Panescu et al. | |
| 6,813,520 B2 | 11/2004 | Truckai et al. | |

(Continued)

OTHER PUBLICATIONS

Third party observations dated Sep. 6, 2013 for EP Application No. 10830743.0.

*Primary Examiner* — Ophelia A Hawthorne
(74) *Attorney, Agent, or Firm* — Wilson Sonsini Goodrich & Rosati

(57) ABSTRACT

An endocervical seal has a sleeve with a passageway for receiving an intrauterine interventional or diagnostic tool. The sleeve has a coaxially disposed outer balloon with a distal portion configured to inflate in a cervical os and a proximal portion configured to inflate in a cervical canal.

5 Claims, 22 Drawing Sheets

(56) References Cited

U.S. PATENT DOCUMENTS

| | | | |
|---|---|---|---|
| 7,371,231 B2* | 5/2008 | Rioux | A61B 18/14 |
| | | | 606/32 |
| 8,641,621 B2* | 2/2014 | Razzaque | A61B 19/5244 |
| | | | 600/407 |
| 2005/0143728 A1 | 6/2005 | Sampson et al. | |
| 2005/0240211 A1* | 10/2005 | Sporri | A61B 17/42 |
| | | | 606/193 |
| 2006/0235461 A1* | 10/2006 | Harter | A61B 17/42 |
| | | | 606/193 |
| 2006/0271092 A1* | 11/2006 | Reed | A61M 29/02 |
| | | | 606/193 |
| 2008/0097425 A1 | 4/2008 | Truckai | |
| 2008/0167664 A1 | 7/2008 | Payne et al. | |
| 2009/0054892 A1 | 2/2009 | Rioux et al. | |
| 2009/0157068 A1* | 6/2009 | Kallel | A61B 18/1492 |
| | | | 606/33 |

* cited by examiner

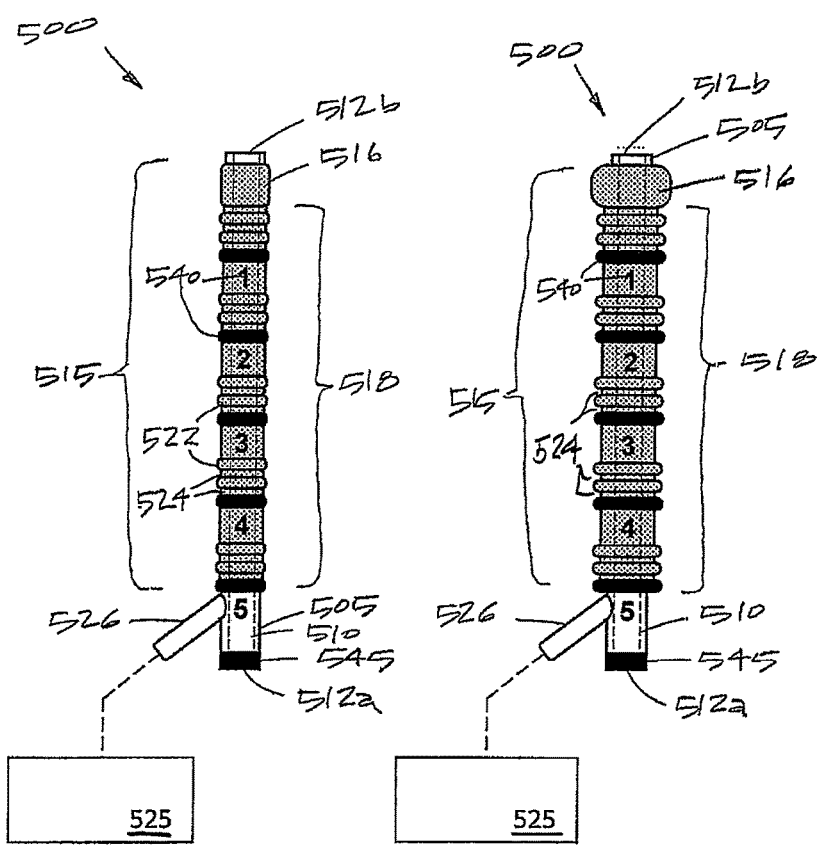
FIG. 14A   FIG. 14B

SYSTEMS AND METHODS FOR ENDOMETRIAL ABLATION

CROSS REFERENCE TO RELATED APPLICATIONS

This application claims the benefit of Provisional Application No. 61/570,144, filed Dec. 13, 2011, the full disclosure of which is incorporated herein by reference.

BACKGROUND

1. Field of the Invention

The present invention relates to electrosurgical methods and devices for global endometrial ablation in a treatment of menorrhagia. More particularly, the present invention relates to applying radiofrequency current to endometrial tissue by means of capacitively coupling the current through an expandable, thin-walled dielectric member enclosing an ionized gas.

A variety of devices have been developed or proposed for endometrial ablation. Of relevance to the present invention, a variety of radiofrequency ablation devices have been proposed including solid electrodes, balloon electrodes, metallized fabric electrodes, and the like. While often effective, many of the prior electrode designs have suffered from one or more deficiencies, such as relatively slow treatment times, incomplete treatments, non-uniform ablation depths, and risk of injury to adjacent organs.

For these reasons, it would be desirable to provide systems and methods that allow for endometrial ablation using radiofrequency current which is rapid, provides for controlled ablation depth and which reduce the risk of injury to adjacent organs. At least some of these objectives will be met by the invention described herein.

2. Description of the Background Art

U.S. Pat. Nos. 5,540,658 and 5,653,692 describe intrauterine ablation devices with cervical seals. U.S. Pat. Nos. 5,769,880; 6,296,639; 6,663,626; and 6,813,520 describe intrauterine ablation devices formed from a permeable mesh defining electrodes for the application of radiofrequency energy to ablate uterine tissue. U.S. Pat. No. 4,979,948 describes a balloon filled with an electrolyte solution for applying radiofrequency current to a mucosal layer via capacitive coupling. US 2008/097425, having common inventorship with the present application, describes delivering a pressurized flow of a liquid medium which carries a radiofrequency current to tissue, where the liquid is ignited into a plasma as it passes through flow orifices. U.S. Pat. No. 5,891,134 describes a radiofrequency heater within an enclosed balloon. U.S. Pat. No. 6,041,260 describes radiofrequency electrodes distributed over the exterior surface of a balloon which is inflated in a body cavity to be treated. U.S. Pat. No. 7,371,231 and US 2009/054892 describe a conductive balloon having an exterior surface which acts as an electrode for performing endometrial ablation. U.S. Pat. No. 5,191,883 describes bipolar heating of a medium within a balloon for thermal ablation. U.S. Pat. Nos. 6,736,811 and 5,925,038 show an inflatable conductive electrode.

BRIEF SUMMARY OF THE INVENTION

The present invention provides methods, systems and devices for sealing of the cervix or cervical canal, for example as part of a uterine access, ablation, or other therapeutic or diagnostic procedure. The methods and systems may also provide for evaluation of the integrity of a uterine cavity. The uterine cavity may be perforated or otherwise damaged by the transcervical introduction of probes and instruments into the uterine cavity. If the uterine wall is perforated, it would be preferable to defer any ablation treatment until the uterine wall is healed.

Embodiments herein provide a system for treating uterine tissue, comprising an expandable RF energy delivery surface for positioning in a uterine cavity; an RF source configured to deliver current across the surface; and a sealing structure disposed adjacent the energy delivery surface and configured for positioning in and sealing a cervical canal.

The sealing structure may be, for example, an elongated bellows-like member with a compliant wall. In embodiments, the sealing structure has a longitudinal axis, and has a repose state with a plurality of annular ridges for engaging tissue surrounding a cervical canal. The sealing structure can be axially stretched to provide a reduced cross section for insertion in the patient's uterine canal.

In further embodiments, the sealing structure is elongated with a distal portion having a greater cross section in a repose state, and a proximal portion with a lesser cross section in a repose state.

The sealing structure may be carried concentrically around a distal portion of a sleeve assembly or support member that carries the RF energy delivery surface of the endometrial ablation system.

In embodiments, the energy delivery surface comprises a wall surrounding an interior chamber. The wall may include at least partly a dielectric. The wall may further include an electrode. The interior chamber may be fluid-tight.

In accordance with still further embodiments, a method of treating uterine tissue is provided, comprising expanding a RF energy delivery surface within a patient's uterine cavity; expanding an expandable member in the patient's cervical canal; and activating an RF source configured to deliver current across the surface to ablate endometrial tissue.

In further embodiments, expanding the RF energy delivery surface comprises expanding a frame supporting the surface.

Systems according to the present invention for transcervical introduction to a patient's uterus comprise a radially expanding sleeve and a probe shaft. The radially expanding sleeve has a proximal end, a distal end, and a central passage between said ends. The sleeve is adapted to be introduced into the cervix or cervical canal in a reduced width configuration and to be immobilized within the cervical canal in an expanded width configuration. The probe shaft is slideably received in the central passage of the sleeve so that the shaft may be advanced, retracted, and otherwise manipulated within the central passage while the sleeve remains immobilized in the cervix or cervical canal, typically during a therapeutic or diagnostic procedure, more typically during a uterine ablation procedure. Such sealing of the cervix and/or cervical canal can inhibit and preferably prevent thermal or other damage from occurring during the procedure. Sealing the cervix and/or cervical canal with a sleeve that can remain immobilized during the procedure is particularly advantageous since it allows the therapeutic, diagnostic, or other device associated with the probe shaft to be repositioned and otherwise manipulated during the procedure while minimizing the risk of disturbing the protective seal. While prior devices have had seals affixed to the therapeutic device, such fixed seals are more likely to be dislodged during performance of the therapeutic and/or diagnostic procedure.

In specific embodiments of the systems of the present invention, the sleeve includes a proximal collar with a locking mechanism which can selectively lock and unlock the sleeve to the probe shaft. With such a locking mechanism, the physician is able to optimally position the probe and at least temporarily lock the probe relative to the sleeve to inhibit subsequent dislodgement or movement of the probe during remaining portions or segments of the protocol. For example, when performing uterine ablation procedures, it may be desirable to immobilize the sleeve in the cervix, position a thermal or other treatment element on the probe shaft within the uterus (while the sleeve remains immobilized), lock the probe shaft to the sleeve once the thermal ablation element has been properly positioned, and then perform thermal ablation while the thermal ablation element remains stabilized in the appropriate position by its attachment to the sleeve which is immobilized in the cervix. Locking mechanism may comprise any suitable latch, lock, anchor, or other device which can be selectively engaged to fix the probe to the sleeve and then selectively disengaged to release the probe so that it can again be moved relative to the sleeve.

In further specific examples, the sleeve may comprise a variety of specific features which enable it to be preferentially locked within the cervix or cervical canal. For example, the sleeve may comprise a distal balloon which can be inflated to engage an interior surface of the uterus or a posterior surface of the cervical os, where the balloon may be part of or separate from a mechanism or segment which locks the sleeve within the cervical canal itself. The sleeve may, for example, comprise a tubular assembly having a deformable thin-walled seal disposed over the tubular assembly, where the seal is configured for axial deformation between a first transversally expanded shaped for engaging the cervical canal and a second transversally non-expanded shape which permits the sleeve to be transcervically inserted and subsequently removed. Usually, the proximal and distal ends of the seal will be coupled to the tubular assembly, more typically being coupled to first and second concentric tubes which form the tubular assembly, where relative axial movement of the concentric sleeves provides the desired axial deformation of the sleeve (e.g., axially extending or opening the tubes will axially lengthen the sleeve and reduce the sleeve's width. In such embodiments, the sleeve typically comprises an elastomeric material, such as a thin walled silicone elastomer, optionally having helical ridges and valley regions which form upon axial shortening. In addition to deforming the sleeve in response to axial extension and compression, the systems may further comprise a pressurized fluid source which is connected to the tubular assembly to selectively inflate the deformable thin-walled seal when the seal is already in its transversally expanded shape. In such inflatable embodiments, the deformable thin-walled seal will have annular or helical first and second regions having first and second durometers, respectively, with the region having a higher durometer than the second region. The pressurized fluid from the source will be connected to apply to the seal to expand the second region but not the first region, as controlled by respective durometers of the regions. In a specific embodiment, the deformable thin-walled seal has a stretched (low profile or width) cross-section for transcervical insertion and a non-stretched (expanded width) cross-section for sealing the cervical canal. In these embodiments, the seal contains a fluid-tight interior chamber having a wall with annular or helical regions configured for differential transverse expansion upon inflation. The embodiments will also have a pressurized fluid source communicating with the interior chamber, where fluid from the pressurized fluid source differentially inflates the seal to expand the annular or helical regions while the valleys between the ridges may be reinforced or otherwise inhibited from radially expanding.

The present invention further provides methods for accessing a patient's uterus. The methods comprise immobilizing a sleeve in the patient's cervix or cervical canal where the sleeve has a central passage. A probe shaft is repositioned within the central passage while the sleeve remains immobilized, thus allowing the physician to position or reposition a diagnostic or therapeutic tool on the shaft within the uterus while minimizing the risk of disrupting the seal to the cervix. The sleeve may be initially introduced to the cervical canal while the probe is present in the central passage or, alternatively, the sleeve may be positioned without the sleeve being present. In the latter case, the sleeve will be advanced through the probe after the seal has been immobilized. Both cases, the sleeve is typically immobilized by radially expanding a wall or exterior portion of the sleeve within the cervical canal. Expansion of the sleeve may be achieved by causing or allowing the sleeve to axially foreshorten and/or by inflating at least a portion of the wall of the sleeve. Optionally, distal balloon may be inflated or otherwise expanded within the uterine cavity at the distal end of the sleeve. Optionally, the sleeve and the probe shaft may be selectively locked to each other this so that the immobilized sleeve may stabilize the position of a therapeutic or a diagnostic tool on the probe shaft within the uterus. Typically, locking is accomplished by actuating a locking mechanism on the sleeve, usually on a proximal collar of the sleeve which remains accessible to the treating physician during the procedure.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

FIG. 14A is a plan view of a seal assembly for sealing an endocervical canal in a non-expanded position.

FIG. 14B is a plan view of the seal assembly of FIG. 14A in an expanded position.

DETAILED DESCRIPTION

In general, an electrosurgical ablation system is described herein that comprises an elongated introducer member for accessing a patient's uterine cavity with a working end that deploys an expandable thin-walled dielectric structure containing an electrically non-conductive gas as a dielectric. In one embodiment, an interior chamber of the thin-walled dielectric structure contains a circulating neutral gas such as argon. An RF power source provides current that is coupled to the neutral gas flow by a first polarity electrode disposed within the interior chamber and a second polarity electrode at an exterior of the working end. The gas flow, which is converted to a conductive plasma by an electrode arrangement, functions as a switching mechanism that permits current flow to engaged endometrial tissue only when the voltage across the combination of the gas, the thin-walled dielectric structure and the engaged tissue reaches a threshold that causes capacitive coupling across the thin-walled dielectric material. By capacitively coupling current to tissue in this manner, the system provides a substantially uniform tissue effect within all tissue in contact with the expanded dielectric structure. Further, the invention allows the neutral gas to be created contemporaneously with the capacitive coupling of current to tissue.

In general, this disclosure may use the terms "plasma," "conductive gas" and "ionized gas" interchangeably. A plasma consists of a state of matter in which electrons in a neutral gas are stripped or "ionized" from their molecules or atoms. Such plasmas can be formed by application of an electric field or by high temperatures. In a neutral gas, electrical conductivity is non-existent or very low. Neutral gases act as a dielectric or insulator until the electric field reaches a breakdown value, freeing the electrons from the atoms in an avalanche process thus forming a plasma. Such a plasma provides mobile electrons and positive ions, and acts as a conductor which supports electric currents and can form spark or arc. Due to their lower mass, the electrons in a plasma accelerate more quickly in response to an electric field than the heavier positive ions, and hence carry the bulk of the current.

Figure 1:
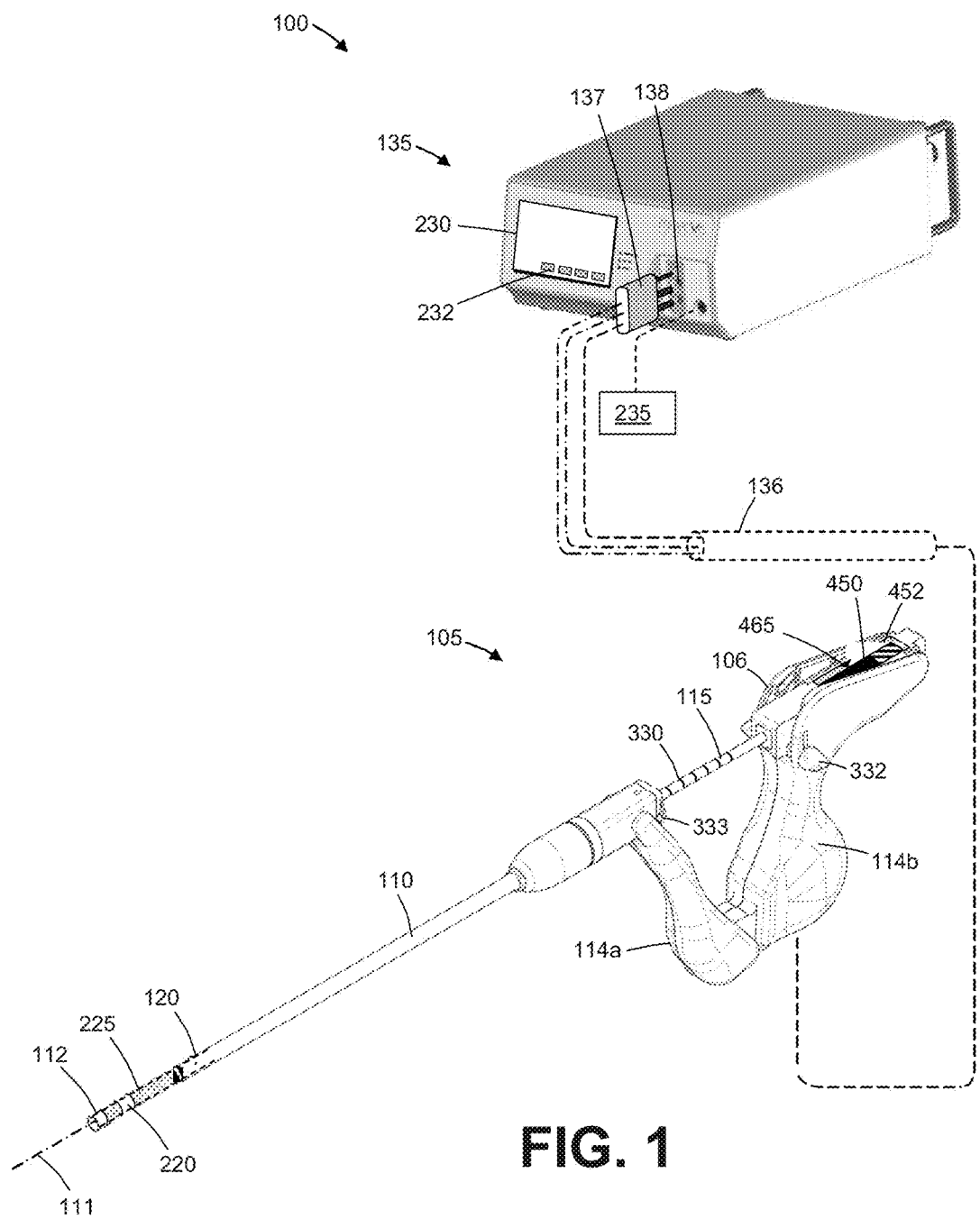
FIG. 1 is a perspective view of an ablation system corresponding to the invention, including a hand-held electrosurgical device for endometrial ablation, RF power source, gas source and controller.
Figure 2:
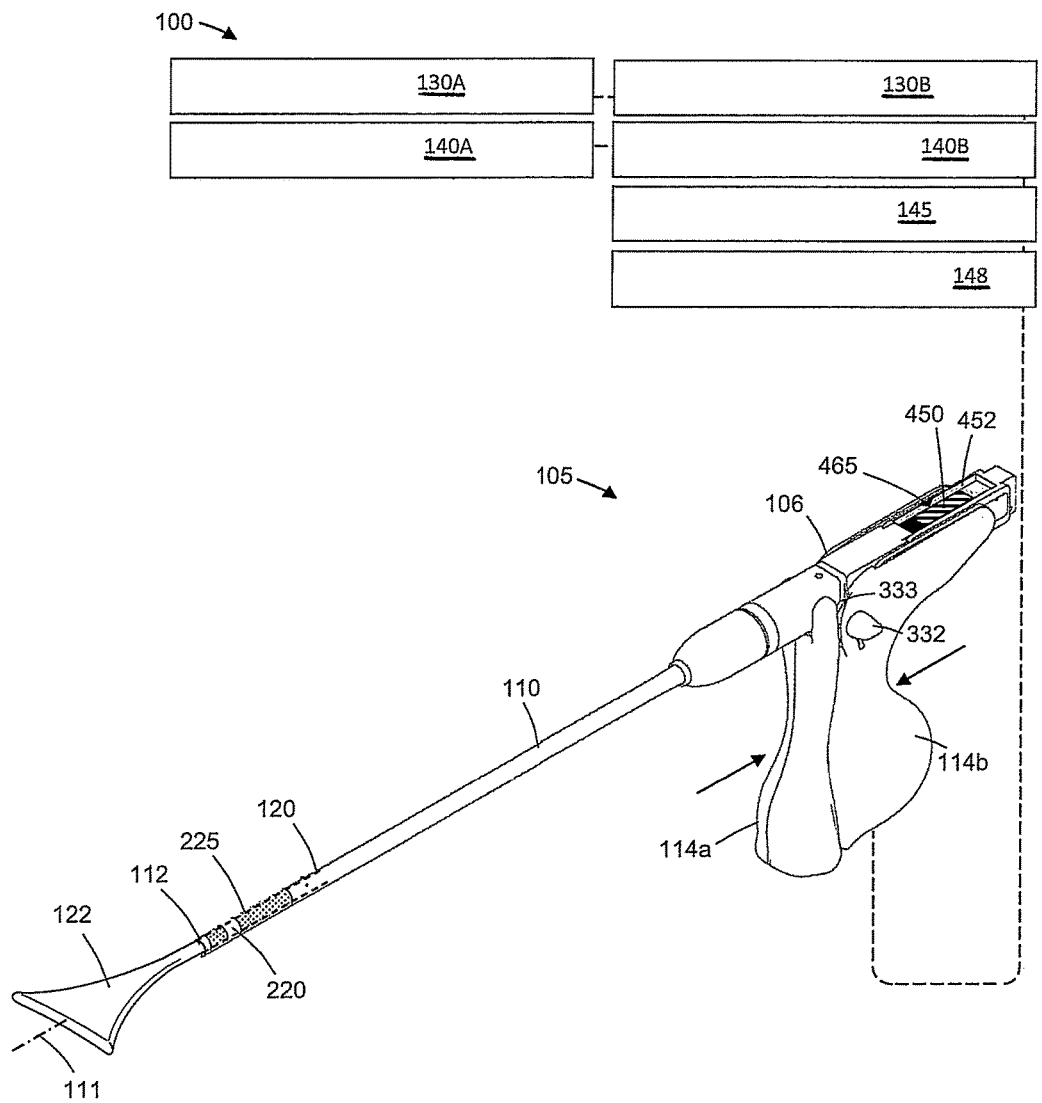
FIG. 2 is a view of the hand-held electrosurgical device of FIG. 1 with a deployed, expanded thin-walled dielectric structure.

FIG. 1 depicts one embodiment of an electrosurgical ablation system 100 configured for endometrial ablation. The system 100 includes a hand-held apparatus 105 with a proximal handle 106 shaped for grasping with a human hand that is coupled to an elongated introducer sleeve 110 having axis 111 that extends to a distal end 112. The introducer sleeve 110 can be fabricated of a thin-walled plastic, composite, ceramic or metal in a round or oval cross-section having a diameter or major axis ranging from about 4 mm to 8 mm in at least a distal portion of the sleeve that accesses the uterine cavity. The handle 106 is fabricated of an electrically insulative material such as a molded plastic with a pistol-grip having first and second portions, 114a and 114b, that can be squeezed toward one another to translate an elongated translatable sleeve 115 which is housed in a bore 120 in the elongated introducer sleeve 110. By actuating the first and second handle portions, 114a and 114b, a working end 122 can be deployed from a first retracted position (FIG. 1) in the distal portion of bore 120 in introducer sleeve 110 to an extended position as shown in FIG. 2. In FIG. 2, it can be seen that the first and second handle portions, 114a and 114b, are in a second actuated position with the working end 122 deployed from the bore 120 in introducer sleeve 110.

Figure 3:
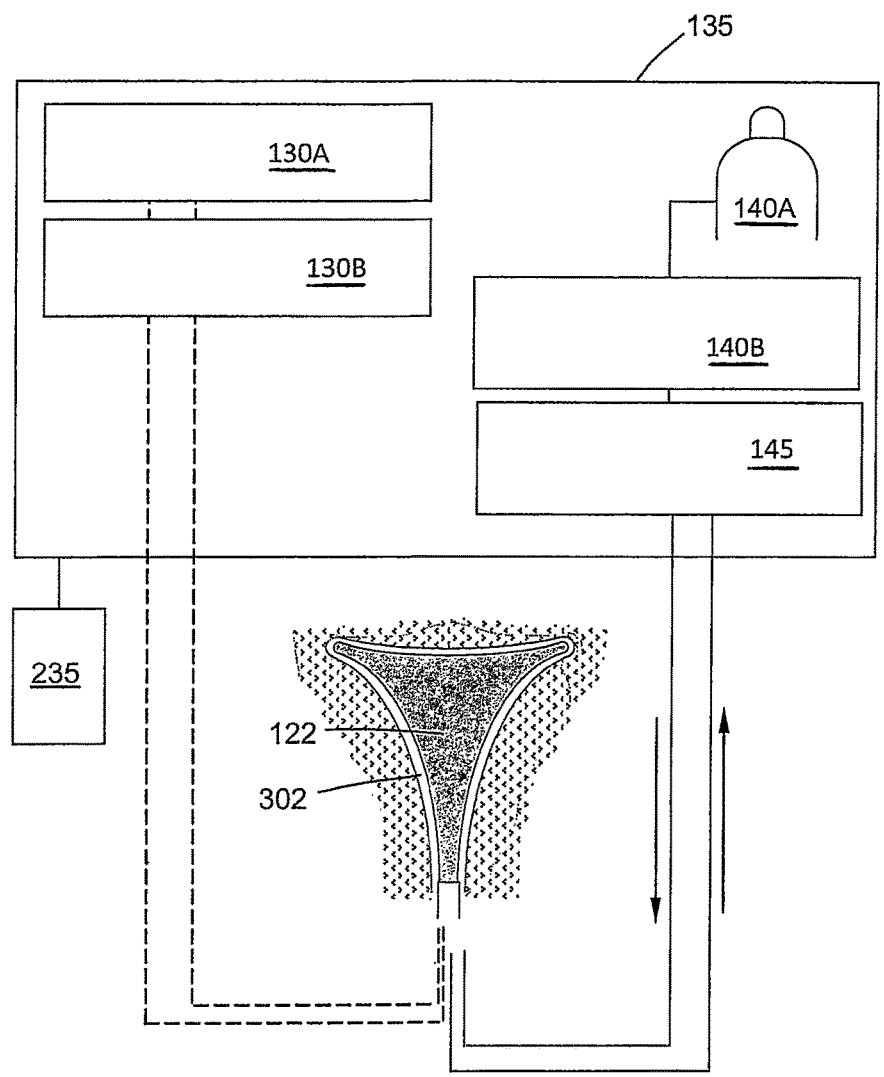
FIG. 3 is a block diagram of components of one electrosurgical system corresponding to the invention.

FIGS. 2 and 3 shows that ablation system 100 includes an RF energy source 130A and RF controller 130B in a control unit 135. The RF energy source 130A is connected to the hand-held device 105 by a flexible conduit 136 with a plug-in connector 137 configured with a gas inflow channel, a gas outflow channel, and first and second electrical leads for connecting to receiving connector 138 in the control unit 135. The control unit 135, as will be described further below in FIGS. 3 and 4, further comprises a neutral gas inflow source 140A, gas flow controller 140B and optional vacuum or negative pressure source 145 to provide controlled gas inflows and gas outflows to and from the working end 122. The control unit 135 further includes a balloon inflation source 148 for inflating an expandable sealing balloon 225 carried on introducer sleeve 110 as described further below.

Referring to FIG. 2, the working end 122 includes a flexible, thin-walled member or structure 150 of a dielectric material that when expanded has a triangular shape configured for contacting the patient's endometrial lining that is targeted for ablation. In one embodiment as shown in FIGS. 2, 5 and 6, the dielectric structure 150 comprises a thin-walled material such as silicone with a fluid-tight interior chamber 152.

In an embodiment, an expandable-collapsible frame assembly 155 is disposed in the interior chamber. Alternatively, the dielectric structure may be expanded by a neutral gas without a frame, but using a frame offers a number of advantages. First, the uterine cavity is flattened with the opposing walls in contact with one another. Expanding a balloon-type member may cause undesirable pain or spasms. For this reason, a flat structure that is expanded by a frame is better suited for deployment in the uterine cavity. Second, in embodiments herein, the neutral gas is converted to a conductive plasma at a very low pressure controlled by gas inflows and gas outflows—so that any pressurization of a balloon-type member with the neutral gas may exceed a desired pressure range and would require complex controls of gas inflows and gas outflows. Third, as described below, the frame provides an electrode for contact with the neutral gas in the interior chamber 152 of the dielectric structure 150, and the frame 155 extends into all regions of the interior chamber to insure electrode exposure to all regions of the neutral gas and plasma. The frame 155 can be constructed of any flexible material with at least portions of the frame functioning as spring elements to move the thin-walled structure 150 from a collapsed configuration (FIG. 1) to an expanded, deployed configuration (FIG. 2) in a patient's uterine cavity. In one embodiment, the frame 155 comprises stainless steel elements 158a, 158b and 160a and 160b that function akin to leaf springs. The frame can be a stainless steel such as 316 SS, 17A SS, 420 SS, 440 SS or the frame can be a NiTi material. The frame preferably extends along a single plane, yet remains thin transverse to the plane, so that the frame may expand into the uterine cavity. The frame elements can have a thickness ranging from about 0.005" to 0.025". As can be seen in FIGS. 5 and 6, the proximal ends 162a and 162b of spring elements 158a, 158b are fixed (e.g., by welds 164) to the distal end 165 of sleeve member 115. The proximal ends 166a and 166b of spring elements 160a, 160b are welded to distal portion 168 of a secondary translatable sleeve 170 that can be extended from bore 175 in translatable sleeve 115. The secondary translatable sleeve 170 is dimensioned for a loose fit in bore 175 to allow gas flows within bore 175. FIGS. 5 and 6 further illustrate the distal ends 176a and 176b of spring elements 158a, 158b are welded to distal ends 178a and 178b of spring elements 160a and 160b to thus provide a frame 155 that can be moved from a linear shape (see FIG. 1) to an expanded triangular shape (FIGS. 5 and 6).

As will be described further below, the bore 175 in sleeve 115 and bore 180 in secondary translatable sleeve 170 function as gas outflow and gas inflow lumens, respectively. It should be appreciated that the gas inflow lumen can comprise any single lumen or plurality of lumens in either sleeve 115 or sleeve 170 or another sleeve, or other parts of the frame 155 or the at least one gas flow lumen can be formed into a wall of dielectric structure 150. In FIGS. 5, 6 and 7 it can be seen that gas inflows are provided through bore 180 in sleeve 170, and gas outflows are provided in bore 175 of sleeve 115. However, the inflows and outflows can be also be reversed between bores 175 and 180 of the various sleeves. FIGS. 5 and 6 further show that a rounded bumper element 185 is provided at the distal end of sleeve 170 to insure that no sharp edges of the distal end of sleeve 170 can contact the inside of the thin dielectric wall 150. In one embodiment, the bumper element 185 is silicone, but it could also comprise a rounded metal element. FIGS. 5 and 6 also show gas inflow indicated by arrows 187 flowing through a plurality of gas inflow ports 188 can be provided along a length of in sleeve 170 in chamber 152, as well as through a port 190 in the distal end of sleeve 170 and bumper element 185. The sectional view of FIG. 7 also shows the gas flow passageways within the interior of introducer sleeve 110.

Figure 5:
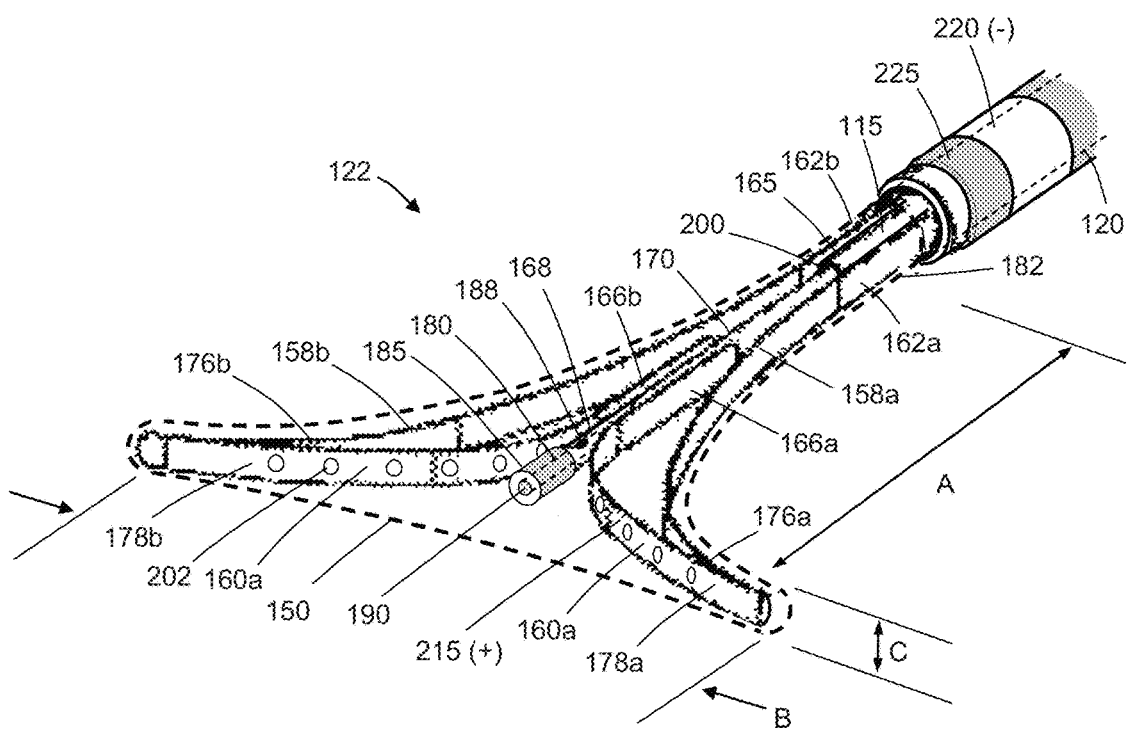
FIG. 5 is an enlarged perspective view of the expanded thin-walled dielectric structure, showing an expandable-collapsible frame with the thin dielectric wall in phantom view.
Figure 6:
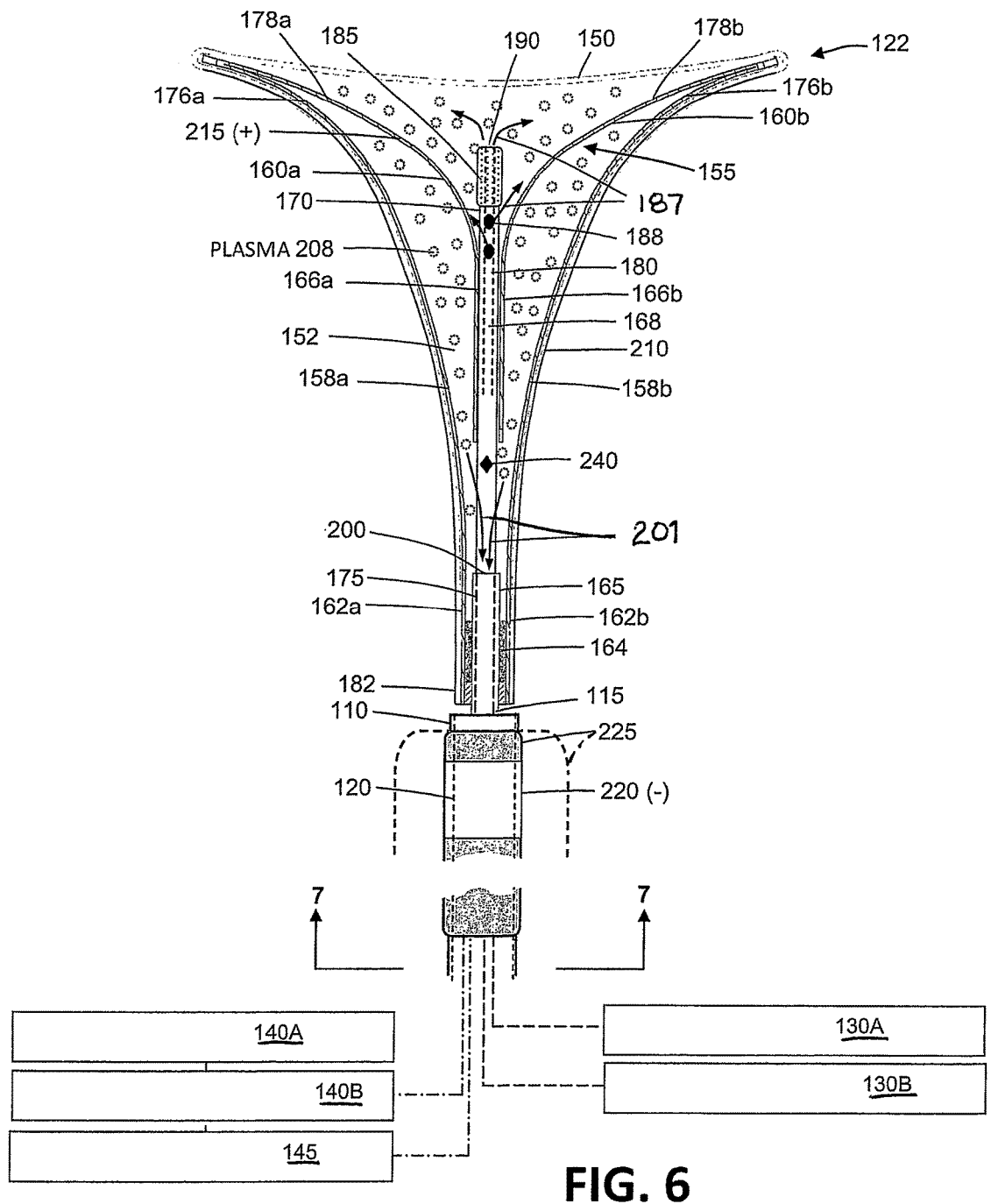
FIG. 6 is a partial sectional view of the expanded thin-walled dielectric structure of FIG. 5 showing (i) translatable members of the expandable-collapsible frame a that move the structure between collapsed and (ii) gas inflow and outflow lumens.
Figure 7:
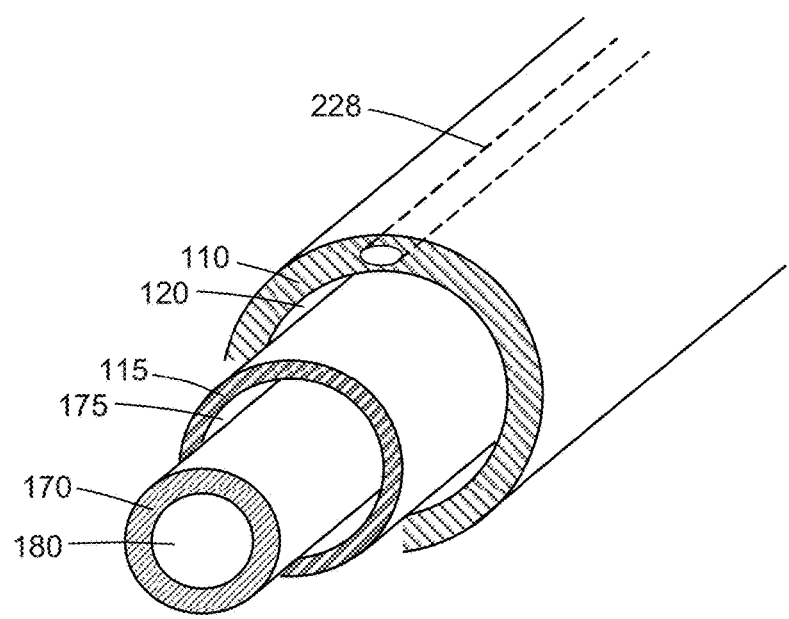
FIG. 7 is a sectional view of an introducer sleeve showing various lumens of the introducer sleeve taken along line 7-7 of FIG. 6.

It can be understood from FIGS. 1, 2, 5 and 6 that actuation of first and second handle portions, 114a and 114b, (i) initially causes movement of the assembly of sleeves 115 and 170 relative to bore 120 of introducer sleeve 110, and (ii) secondarily causes extension of sleeve 170 from bore 175 in sleeve 115 to expand the frame 155 into the triangular shape of FIG. 5. The dimensions of the triangular shape are suited for a patient uterine cavity, and for example can have an axial length A ranging from 4 to 10 cm and a maximum width B at the distal end ranging from about 2 to 5 cm. In one embodiment, the thickness C of the thin-walled structure 150 can be from 1 to 4 mm as determined by the dimensions of spring elements 158a, 158b, 160a and 160b of frame assembly 155. It should be appreciated that the frame assembly 155 can comprise round wire elements, flat spring elements, of any suitable metal or polymer that can provide opening forces to move thin-walled structure 150 from a collapsed configuration to an expanded configuration within the patient uterus. Alternatively, some elements of the frame 155 can be spring elements and some elements can be flexible without inherent spring characteristics.

As will be described below, the working end embodiment of FIGS. 2, 5 and 6 has a thin-walled structure 150 that is formed of a dielectric material such as silicone that permits capacitive coupling of current to engaged tissue while the frame assembly 155 provides structural support to position the thin-walled structure 150 against tissue. Further, gas inflows into the interior chamber 152 of the thin-walled structure can assist in supporting the dielectric wall so as to contact endometrial tissue. The dielectric thin-walled structure 150 can be free from fixation to the frame assembly 155, or can be bonded to an outward-facing portion or portions of frame elements 158a and 158b. The proximal end 182 of thin-walled structure 150 is bonded to the exterior of the distal end of sleeve 115 to thus provide a sealed, fluid-tight interior chamber 152 (FIG. 5).

In one embodiment, the gas inflow source 140A comprises one or more compressed gas cartridges that communicate with flexible conduit 136 through plug-in connector 137 and receiving connector 138 in the control unit 135 (FIGS. 1-2). As can be seen in FIGS. 5-6, the gas inflows from source 140A flow through bore 180 in sleeve 170 to open terminations 188 and 190 therein to flow into interior chamber 152. A vacuum source 145 is connected through conduit 136 and connector 137 to allow circulation of gas flow through the interior chamber 152 of the thin-walled dielectric structure 150. In FIGS. 5 and 6, it can be seen that gas outflows communicate with vacuum source 145 through open end 200 of bore 175 in sleeve 115. Referring to FIG. 5, it can be seen that frame elements 158a and 158b are configured with a plurality of apertures 202 to allow for gas flows through all interior portions of the frame elements, and thus gas inflows from open terminations 188, 190 in bore 180 are free to circulated through interior chamber 152 to return to an outflow path through open end 200 of bore 175 of sleeve 115 as indicated by arrows 201. As will be described below (see FIGS. 3-4), the gas inflow source 140A is connected to a gas flow or circulation controller 140B which controls a pressure regulator 205 and also controls vacuum source 145 which is adapted for assisting in circulation of the gas. It should be appreciated that the frame elements can be configured with apertures, notched edges or any other configurations that allow for effective circulation of a gas through interior chamber 152 of the thin-walled structure 150 between the inflow and outflow passageways.

Now turning to the electrosurgical aspects of the invention, FIGS. 5 and 6 illustrate opposing polarity electrodes of the system 100 that are configured to convert a flow of neutral gas in chamber 152 into a plasma 208 (FIG. 6) and to allow capacitive coupling of current through a wall 210 of the thin-walled dielectric structure 150 to endometrial tissue in contact with the wall 210. The electrosurgical methods of capacitively coupling RF current across a plasma 208 and dielectric wall 210 are described in U.S. patent application Ser. No. 12/541,043; filed Aug. 13, 2009 and U.S. application Ser. No. 12/541,050, referenced above. In FIGS. 5 and 6, the first polarity electrode 215 is within interior chamber 152 to contact the neutral gas flow and comprises the frame assembly 155 that is fabricated of an electrically conductive stainless steel. In another embodiment, the first polarity electrode can be any element disposed within the interior chamber 152, or extendable into interior chamber 152. The first polarity electrode 215 is electrically coupled to sleeves 115 and 170 which extends through the introducer sleeve 110 to handle 106 and conduit 136 and is connected to a first pole of the RF source energy source 130A and controller 130B. A second polarity electrode 220 is external of the internal chamber 152 and in one embodiment the electrode is spaced apart from wall 210 of the thin-walled dielectric structure 150. In one embodiment as depicted in FIGS. 5 and 6, the second polarity electrode 220 comprises a surface element of an expandable balloon member 225 carried by introducer sleeve 110. The second polarity electrode 220 is coupled by a lead (not shown) that extends through the introducer sleeve 110 and conduit 136 to a second pole of the RF source 130A. It should be appreciated that second polarity electrode 220 can be positioned on sleeve 110 or can be attached to surface portions of the expandable thin-walled dielectric structure 150, as will be described below, to provide suitable contact with body tissue to allow the electrosurgical ablation of the method of the invention. The second polarity electrode 220 can comprise a thin conductive metallic film, thin metal wires, a conductive flexible polymer or a polymeric positive temperature coefficient material. In one embodiment depicted in FIGS. 5 and 6, the expandable member 225 comprises a thin-walled compliant balloon having a length of about 1 cm to 6 cm that can be expanded to seal the cervical canal. The balloon 225 can be inflated (as shown in broken line) with a gas or liquid by any inflation source 148, and can comprise a syringe mechanism controlled manually or by control unit 135. The balloon inflation source 148 is in fluid communication with an inflation lumen 228 in introducer sleeve 110 that extends to an inflation chamber of balloon 225 (see FIG. 7).

Referring back to FIG. 1, the control unit 135 can include a display 230 and touch screen or other controls 232 for setting and controlling operational parameters such as treatment time intervals, treatment algorithms, gas flows, power levels and the like. Suitable gases for use in the system include argon, other noble gases and mixtures thereof. In one embodiment, a footswitch 235 is coupled to the control unit 135 for actuating the system.

Figure 4:
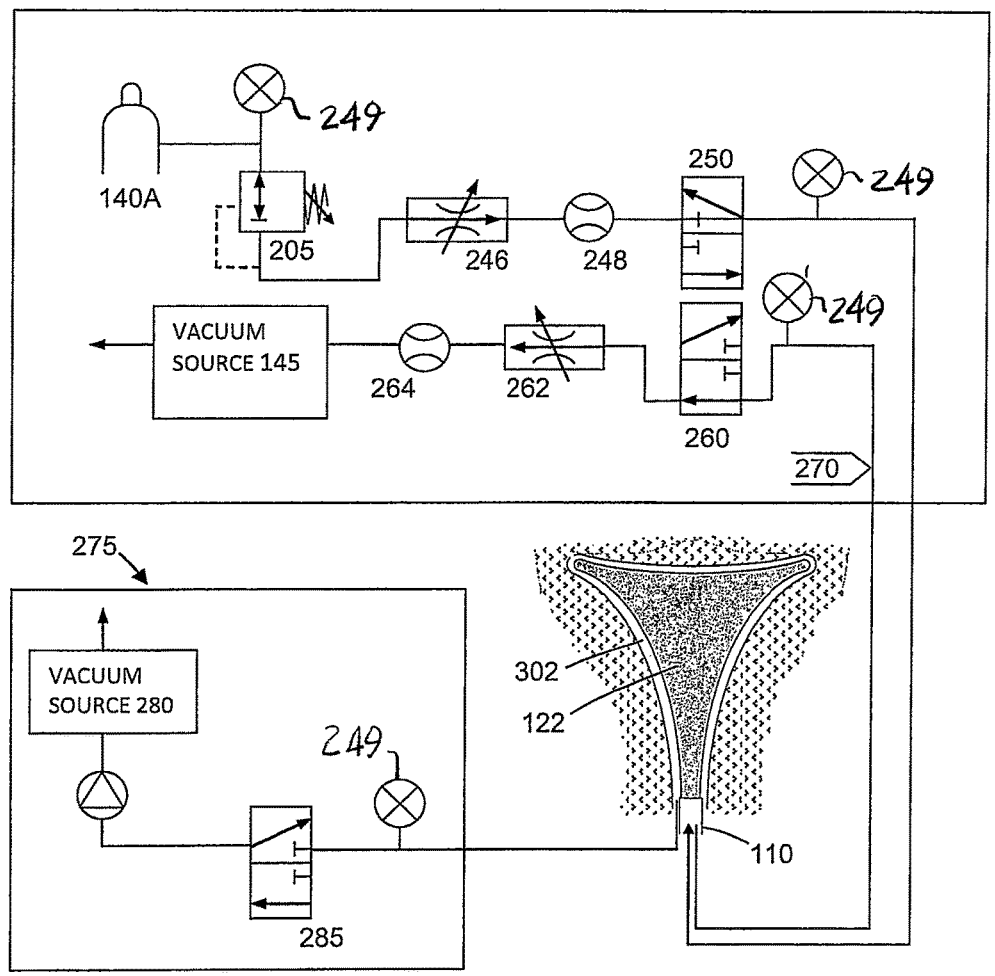
FIG. 4 s a block diagram of the gas flow components of the electrosurgical system of FIG. 1.

The box diagrams of FIGS. 3 and 4 schematically depict the system 100, subsystems and components that are configured for an endometrial ablation system. In the box diagram of FIG. 3, it can be seen that RF energy source 130A and circuitry is controlled by a controller 130B. The system can include feedback control systems that include signals relating to operating parameters of the plasma in interior chamber 152 of the dielectric structure 150. For example, feedback signals can be provided from at least one temperature sensor 240 in the interior chamber 152 of the dielectric structure 150, from a pressure sensor within, or in communication, with interior chamber 152, and/or from a gas flow rate sensor in an inflow or outflow channel of the system. FIG. 4 is a schematic block diagram of the flow control components relating to the flow of gas media through the system 100 and hand-held device 105. It can be seen that a pressurized gas source 140A is linked to a downstream pressure regulator 205, an inflow proportional valve 246, flow meter 248 and normally closed solenoid valve 250. The valve 250 is actuated by the system operator which then allows a flow of a neutral gas from gas source 140A to circulate through flexible conduit 136 and the device 105. The gas outflow side of the system includes a normally open solenoid valve 260, outflow proportional valve 262 and flow meter 264 that communicate with vacuum pump or source 145. The gas can be exhausted into the environment or into a containment system. A temperature sensor 270 (e.g., thermocouple) is shown in FIG. 4 that is configured for monitoring the temperature of outflow gases. FIG. 4 further depicts an optional subsystem 275 which comprises a vacuum source 280 and solenoid valve 285 coupled to the controller 140B for suctioning steam from a uterine cavity 302 at an exterior of the dielectric structure 150 during a treatment interval. As can be understood from FIG. 4, the flow passageway from the uterine cavity 302 can be through bore 120 in sleeve 110 (see FIGS. 2, 6 and 7) or another lumen in a wall of sleeve 110 can be provided. Pressure gauges 249 may be provided at various locations in the system.

FIGS. 8A-8D schematically illustrate a method of the invention wherein (i) the thin-walled dielectric structure 150 is deployed within a patient uterus and (ii) RF current is applied to a contained neutral gas volume in the interior chamber 152 to contemporaneously create a plasma 208 in the chamber and capacitively couple current through the thin dielectric wall 210 to apply ablative energy to the endometrial lining to accomplish global endometrial ablation.

Figure 8A:
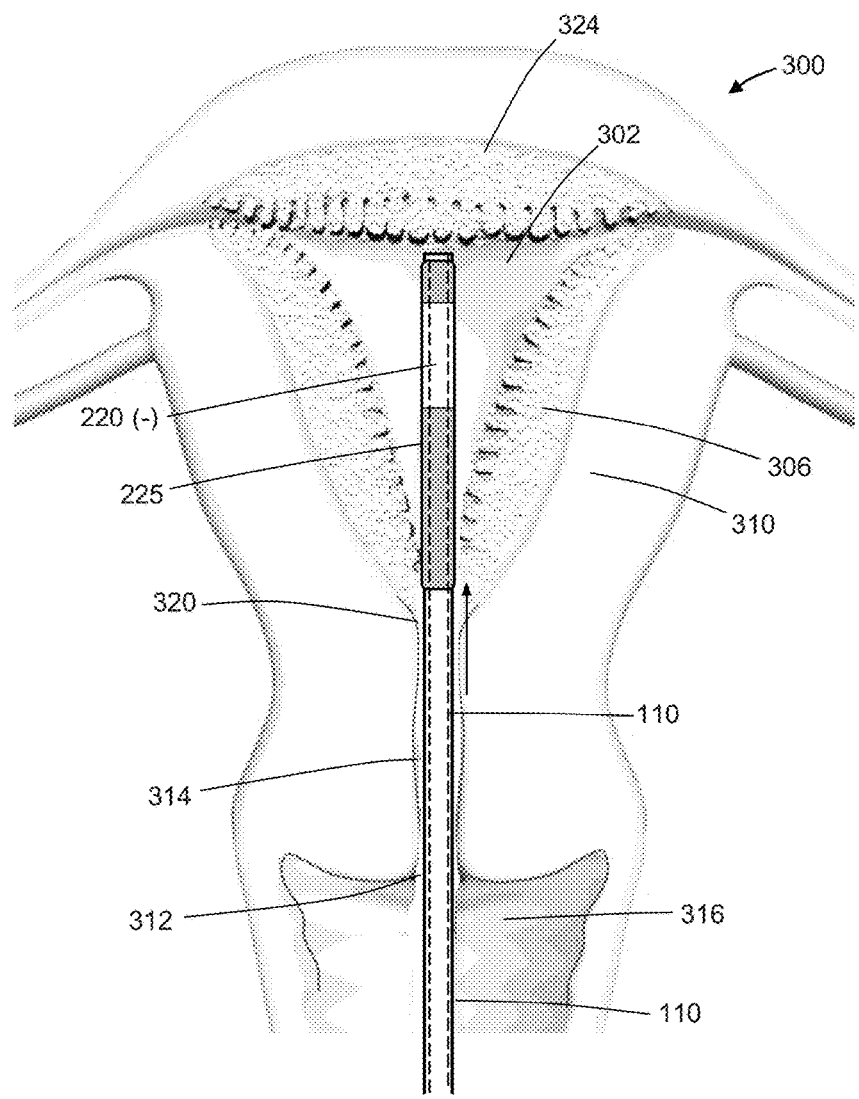
FIG. 8A is an enlarged schematic view of an aspect of a method of the invention illustrating the step introducing an introducer sleeve into a patient's uterus.

More in particular, FIG. 8A illustrates a patient uterus 300 with uterine cavity 302 surrounded by endometrium 306 and myometrium 310. The external cervical os 312 is the opening of the cervix 314 into the vagina 316. The internal os or opening 320 is a region of the cervical canal that opens to the uterine cavity 302. FIG. 8A depicts a first step of a method of the invention wherein the physician has introduced a distal portion of sleeve 110 into the uterine cavity 302. The physician gently can advance the sleeve 110 until its distal tip contacts the fundus 324 of the uterus. Prior to insertion of the device, the physician can optionally introduce a sounding instrument into the uterine cavity to determine uterine dimensions, for example from the internal os 320 to fundus 324.

Figure 8B:
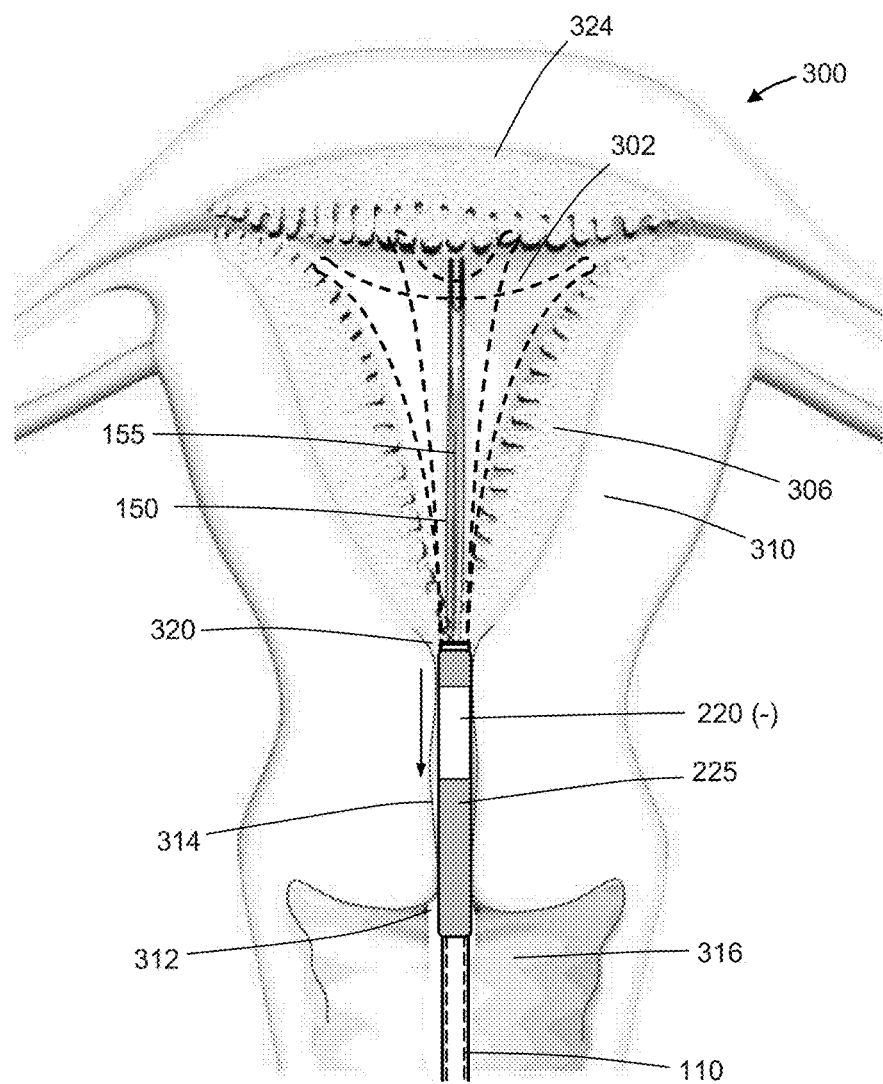
FIG. 8B is a schematic view of a subsequent step of retracting the introducer sleeve to expose a collapsed thin-walled dielectric structure and internal frame in the uterine cavity.

FIG. 8B illustrates a subsequent step of a method of the invention wherein the physician begins to actuate the first and second handle portions, 114a and 114b, and the introducer sleeve 110 retracts in the proximal direction to expose the collapsed frame 155 and thin-walled structure 150 within the uterine cavity 302. The sleeve 110 can be retracted to expose a selected axial length of thin-walled dielectric structure 150, which can be determined by markings 330 on sleeve 115 (see FIG. 1) which indicate the axial travel of sleeve 115 relative to sleeve 170 and thus directly related to the length of deployed thin-walled structure 150. FIG. 2 depicts the handle portions 114a and 114b fully approximated thus deploying the thin-walled structure to its maximum length.

In FIG. 8B, it can be understood that the spring frame elements 158a, 158b, 160a and 160b move the dielectric structure 150 from a non-expanded position to an expanded position in the uterine cavity as depicted by the profiles in dashed lines. The spring force of the frame 155 will expand the dielectric structure 150 until limited by the dimensions of the uterine cavity.

Figure 8C:
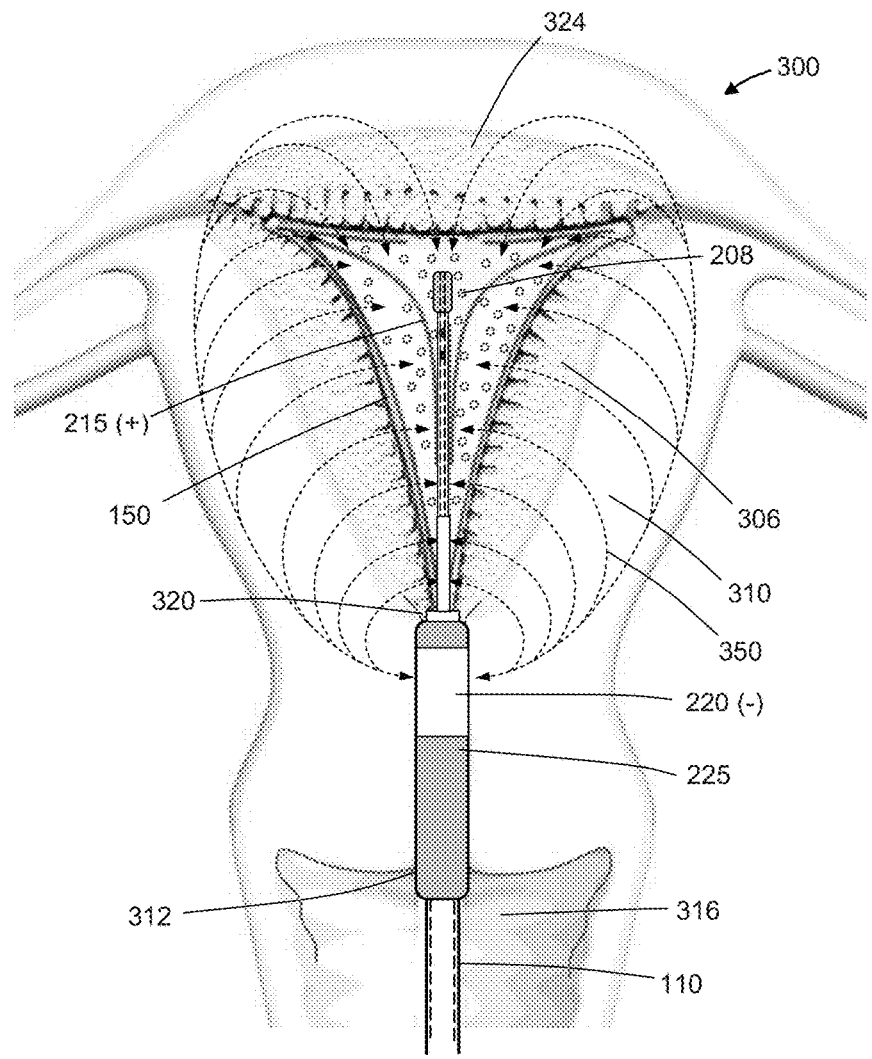
FIG. 8C is a schematic view of subsequent steps of the method, including, (i) actuating the internal frame to move the a collapsed thin-walled dielectric structure to an expanded configuration, (ii) inflating a cervical-sealing balloon carried on the introducer sleeve, and (iii) actuating gas flows and applying RF energy to contemporaneously ionize the gas in the interior chamber and cause capacitive coupling of current through the thin-walled dielectric structure to cause ohmic heating in the engaged tissue indicated by current flow paths.

FIG. 8C illustrates several subsequent steps of a method of the invention. FIG. 8C first depicts the physician continuing to actuate the first and second handle portions, 114a and 114b, which further actuates the frame 155 (see FIGS. 5-6) to expand the frame 155 and thin-walled structure 150 to a deployed triangular shape to contact the patient's endometrial lining 306. The physician can slightly rotate and move the expanding dielectric structure 150 back and forth as the structure is opened to insure it is opened to the desired extent. In performing this step, the physician can actuate handle portions, 114a and 114b, a selected degree which causes a select length of travel of sleeve 170 relative to sleeve 115 which in turn opens the frame 155 to a selected degree. The selected actuation of sleeve 170 relative to sleeve 115 also controls the length of dielectric structure deployed from sleeve 110 into the uterine cavity. Thus, the thin-walled structure 150 can be deployed in the uterine cavity with a selected length, and the spring force of the elements of frame 155 will open the structure 150 to a selected triangular shape to contact or engage the endometrium 306. In one embodiment, the expandable thin-walled structure 150 is urged toward and maintained in an open position by the spring force of elements of the frame 155. In the embodiment depicted in FIGS. 1 and 2, the handle 106 includes a locking mechanism with finger-actuated sliders 332 on either side of the handle that engage a grip-lock element against a notch in housing 333 coupled to introducer sleeve 110 (FIG. 2) to lock sleeves 115 and 170 relative to introducer sleeve 110 to maintain the thin-walled dielectric structure 150 in the selected open position.

FIG. 8C further illustrates the physician expanding the expandable balloon structure 225 from inflation source 148 to thus provide an elongated sealing member to seal the cervix 314 outward from the internal os 320. Following deployment of the thin-walled structure 150 and balloon 225 in the cervix 314, the system 100 is ready for the application of RF energy to ablate endometrial tissue 306. FIG. 8C next depicts the actuation of the system 100, for example, by actuating footswitch 235, which commences a flow of neutral gas from source 140A into the interior chamber 152 of the thin-walled dielectric structure 150. Contemporaneous with, or after a selected delay, the system's actuation delivers RF energy to the electrode arrangement which includes first polarity electrode 215 (+) of frame 155 and the second polarity electrode 220 (−) which is carried on the surface of expandable balloon member 225. The delivery of RF energy delivery will instantly convert the neutral gas in interior chamber 152 into conductive plasma 208 which in turn results in capacitive coupling of current through the dielectric wall 210 of the thin-walled structure 150 resulting in ohmic heating of the engaged tissue. FIG. 8C schematically illustrates the multiplicity of RF current paths 350 between the plasma 208 and the second polarity electrode 220 through the dielectric wall 210. By this method, it has been found that ablation depths of three mm to six mm or more can be accomplished very rapidly, for example in 60 seconds to 120 seconds dependent upon the selected voltage and other operating parameters. In operation, the voltage at which the neutral gas inflow, such as argon, becomes conductive (i.e., converted in part into a plasma) is dependent upon a number of factors controlled by the controllers 130B and 140B, including the pressure of the neutral gas, the volume of interior chamber 152, the flow rate of the gas through the chamber 152, the distance between electrode 210 and interior surfaces of the dielectric wall 210, the dielectric constant of the dielectric wall 210 and the selected voltage applied by the RF source 130, all of which can be optimized by experimentation. In one embodiment, the gas flow rate can be in the range of 5 ml/sec to 50 ml/sec. The dielectric wall 210 can comprise a silicone material having a thickness ranging from a 0.005" to 0.015 and having a relative permittivity in the range of 3 to 4. The gas can be argon supplied in a pressurized cartridge which is commercially available. Pressure in the interior chamber 152 of dielectric structure 150 can be maintained between 14 psia and 15 psia with zero or negative differential pressure between gas inflow source 140A and negative pressure or vacuum source 145. The controller is configured to maintain the pressure in interior chamber in a range that varies by less than 10% or less than 5% from a target pressure. The RF power source 130A can have a frequency of 450 to 550 KHz, and electrical power can be provided within the range of 600 Vrms to about 1200 Vrms and about 0.2 Amps to 0.4 Amps and an effective power of 40 W to 100 W. In one method, the control unit 135 can be programmed to delivery RF energy for a preselected time interval, for example, between 60 seconds and 120 seconds. One aspect of a treatment method corresponding to the invention consists of ablating endometrial tissue with RF energy to elevate endometrial tissue to a temperature greater than 45 degrees Celsius for a time interval sufficient to ablate tissue to a depth of at least 1 mm. Another aspect of the method of endometrial ablation of consists of applying radiofrequency energy to elevate endometrial tissue to a temperature greater than 45 degrees Celsius without damaging the myometrium.

Figure 8D:
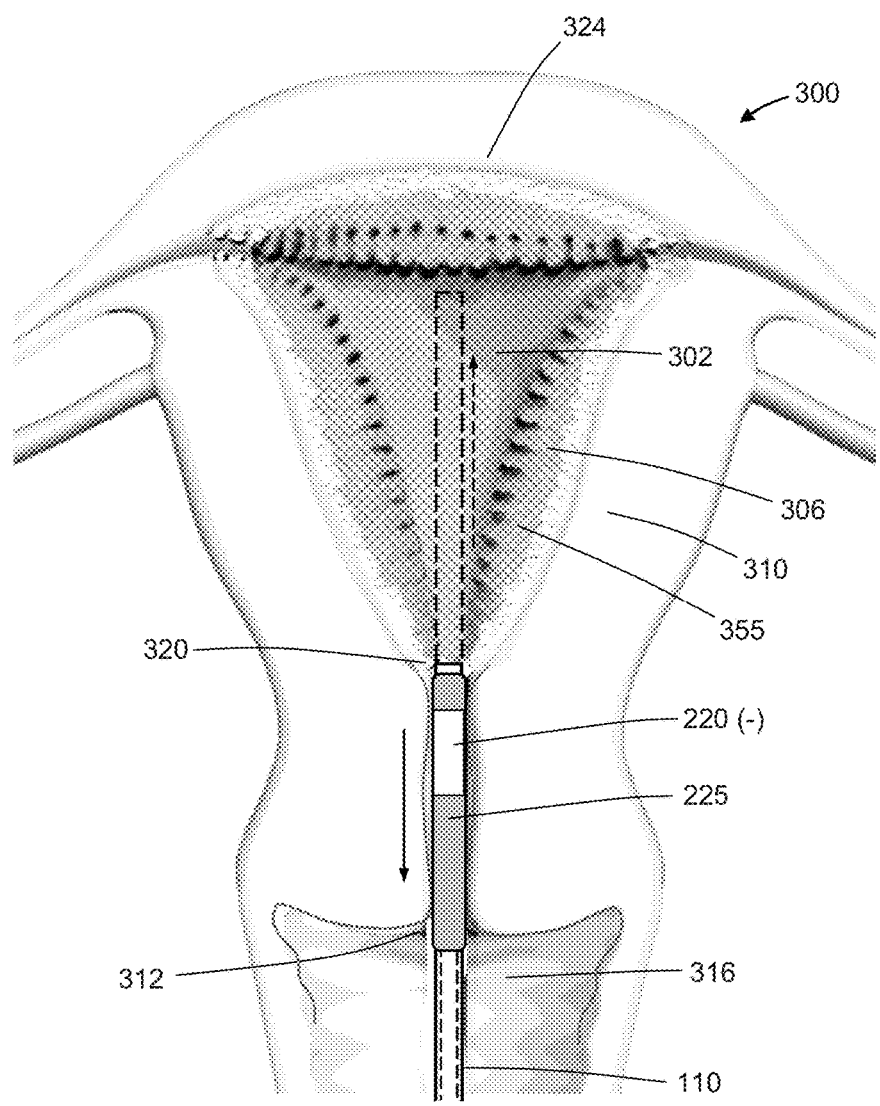
FIG. 8D is a schematic view of a subsequent steps of the method, including: (i) advancing the introducer sleeve over the thin-walled dielectric structure to collapse it into an interior bore shown in phantom view, and (ii) withdrawing the introducer sleeve and dielectric structure from the uterine cavity.

FIG. 8D illustrates a final step of the method wherein the physician deflates the expandable balloon member 225 and then extends sleeve 110 distally by actuating the handles 114a and 114b to collapse frame 155 and then retracting the assembly from the uterine cavity 302. Alternatively, the deployed working end 122 as shown in FIG. 8C can be withdrawn in the proximal direction from the uterine cavity wherein the frame 155 and thin-walled structure 150 will collapse as it is pulled through the cervix. FIG. 8D shows the completed ablation with the ablated endometrial tissue indicated at 360.

In another embodiment, the system can include an electrode arrangement in the handle 106 or within the gas inflow channel to pre-ionize the neutral gas flow before it reaches the interior chamber 152. For example, the gas inflow channel can be configured with axially or radially spaced apart opposing polarity electrodes configured to ionize the gas inflow. Such electrodes would be connected in separate circuitry to an RF source. The first and second electrodes 215 (+) and 220 (−) described above would operate as described above to provide the current that is capacitively coupled to tissue through the walls of the dielectric structure 150. In all other respects, the system and method would function as described above.

Figure 9:
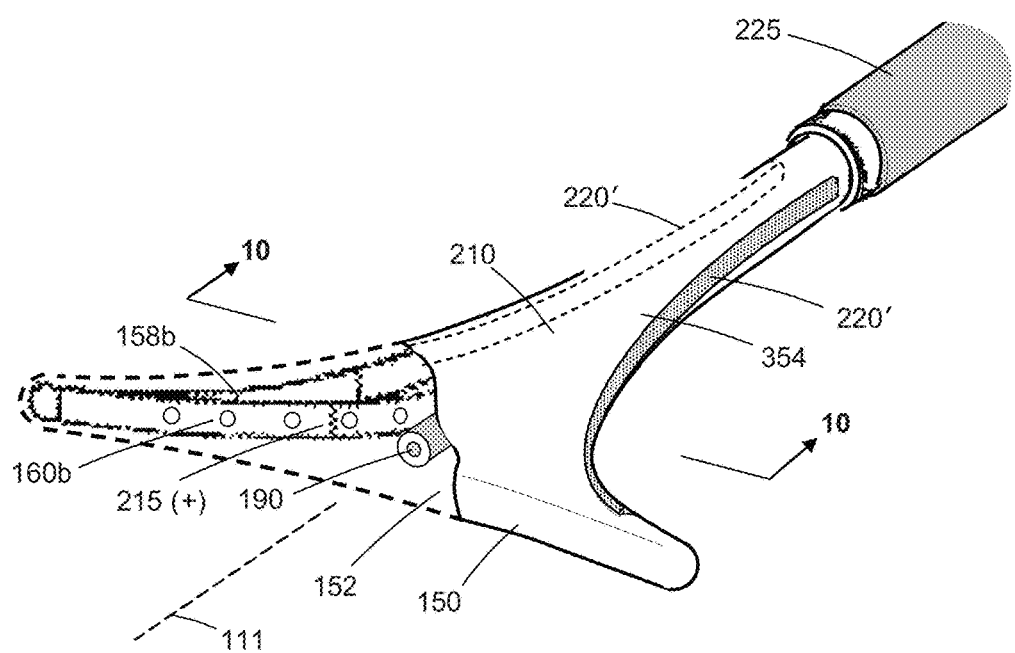
FIG. 9 is a cut-away perspective view of an alternative expanded thin-walled dielectric structure similar to that of FIGS. 5 and 6 show an alternative electrode configuration.
Figure 10:
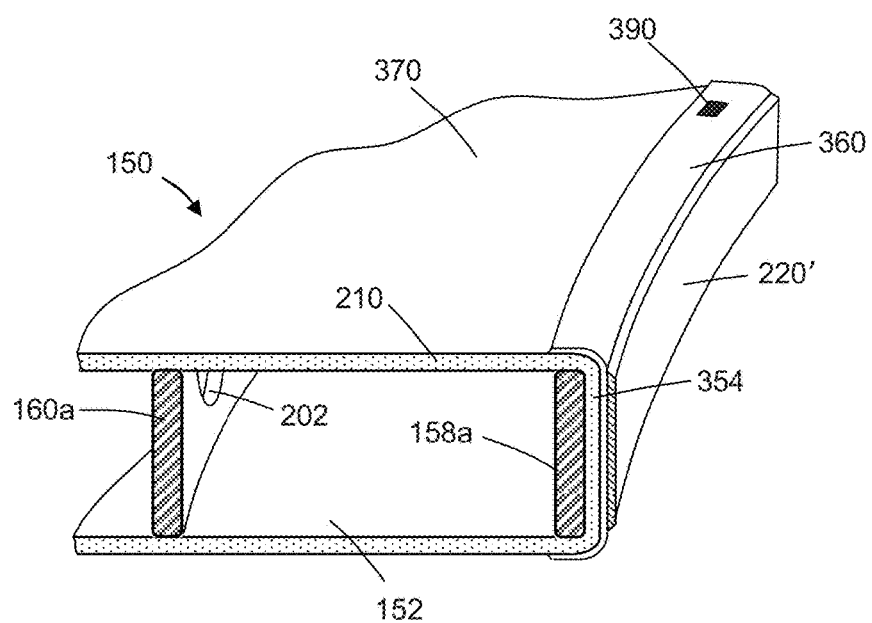
FIG. 10 is an enlarged cut-away view of a portion of the expanded thin-walled dielectric structure of FIG. 9 showing the electrode configuration.

Now turning to FIGS. 9 and 10, an alternate working end 122 with thin-walled dielectric structure 150 is shown. In this embodiment, the thin-walled dielectric structure 150 is similar to that of FIGS. 5 and 6 except that the second polarity electrode 220' that is exterior of the internal chamber 152 is disposed on a surface portion 370 of the thin-walled dielectric structure 150. In this embodiment, the second polarity electrode 220' comprises a thin-film conductive material, such as gold, that is bonded to the exterior of thin-walled material 210 along two lateral sides 354 of dielectric structure 150. It should be appreciated that the second polarity electrode can comprise one or more conductive elements disposed on the exterior of wall material 210, and can extend axially, or transversely to axis 111 and can be singular or multiple elements. In one embodiment shown in more detail in FIG. 10, the second polarity electrode 220' can be fixed on another lubricious layer 360, such as a polyimide film, for example KAPTON®. The polyimide tape extends about the lateral sides 354 of the dielectric structure 150 and provides protection to the wall 210 when it is advanced from or withdrawn into bore 120 in sleeve 110. In operation, the RF delivery method using the embodiment of FIGS. 9 and 10 is the same as described above, with RF current being capacitively coupled from the plasma 208 through the wall 210 and endometrial tissue to the second polarity electrode 220' to cause the ablation.

FIG. 9 further shows an optional temperature sensor 390, such as a thermocouple, carried at an exterior of the dielectric structure 150. In one method of use, the control unit 135 can acquire temperature feedback signals from at least one temperature sensor 390 to modulate or terminate RF energy delivery, or to modulate gas flows within the system. In a related method of the invention, the control unit 135 can acquire temperature feedback signals from temperature sensor 240 in interior chamber 152 (FIG. 6) to modulate or terminate RF energy delivery or to modulate gas flows within the system.

Figure 11:
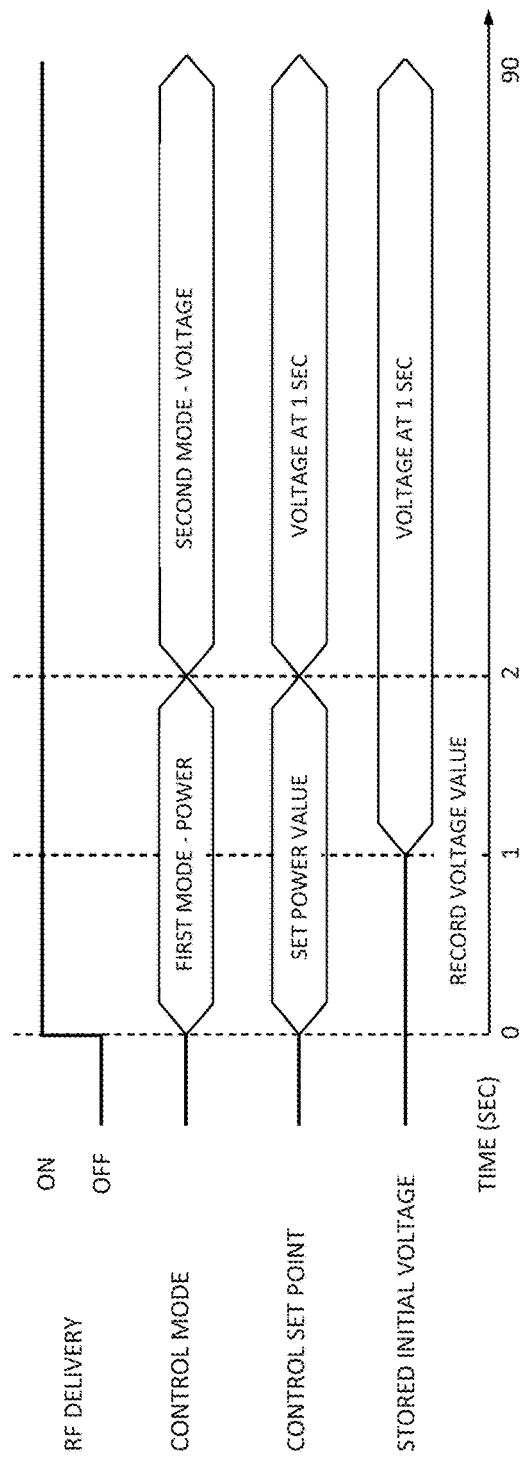
FIG. 11 is a diagram of a radiofrequency energy delivery apparatus and method corresponding to the invention.

In another aspect of the invention, FIG. 11 is a graphic representation of an algorithm utilized by the RF source 130A and RF controller 130B of the system to controllably apply RF energy in an endometrial ablation procedure. In using the expandable dielectric structure 150 of the invention to apply RF energy in an endometrial ablation procedure as described above, the system is configured to allow the dielectric structure 150 to open to different expanded dimensions depending on the size and shape of the uterine cavity 302. The axial length of dielectric structure 150 also can be adjusted to have a predetermined axial length extended outward from the introducer sleeve 110 to match a measured length of a uterine cavity. In any case, the actual surface area of the expanded dielectric structure 150 within different uterine cavities will differ—and it would be optimal to vary total applied energy to correspond to the differing size uterine cavities.

FIG. 11 represents a method of the invention that automatically determines relevant parameters of the tissue and the size of uterine cavity 302 to allow for selection of an energy delivery mode that is well suited to control the total applied energy in an ablation procedure. In embodiments, RF energy is applied at constant power for a first time increment, and the following electrical parameters (e.g., voltage, current, power, impedance) are measured during the application of energy during that first time increment. The measured electrical parameters are then used (principally, power and current, V=P/I) to determine a constant voltage to apply to the system for a second time interval. The initial impedance may be also be utilized by the controller as a shutoff criteria for the second treatment interval after a selected increase in impedance.

For example, in FIG. 11, it can be seen that a first step following the positioning of the dielectric structure in the uterine cavity 302 is to apply radiofrequency energy in a first mode of predetermined constant power, or constant RF energy ("FIRST MODE—POWER"). This first power is sufficient to capacitively couple current across the dielectric to contacted tissue, wherein empirical studies have shown the power can be in the range of 50 W-300 W, and in one embodiment is 80 W. This first power mode is applied for a predetermined interval which can be less than 15 seconds, 10 seconds, or 5 seconds, as examples, and is depicted in FIG. 11 as being 2 seconds. FIG. 11 shows that, in accordance with embodiments, the voltage value is determined a voltage sensor in controller 130A and is recorded at the "one-second" time point after the initiation of RF energy delivery. The controller includes a power sensor, voltage sensor and current sensor as is known in the art. This voltage value, or another electrical parameter, may be determined and recorded at any point during the interval, and more than one recording may be made, with averages taken for the multiple recordings, or the multiple recordings may be used in another way to consistently take a measurement of an electrical value or values. FIG. 11 next illustrates that the controller algorithm switches to a second mode ("SECOND MODE—VOLTAGE") of applying radiofrequency energy at a selected constant voltage, with the selected constant voltage related to the recorded voltage (or other electrical parameter) at the "one-second" time point. In one embodiment, the selected constant voltage is equal to the recorded voltage, but other algorithms can select a constant voltage that is greater or lesser than the recorded voltage but determined by a factor or algorithm applied to the recorded voltage. As further shown in FIG. 11, the algorithm then applies RF energy over a treatment interval to ablate endometrial tissue. During this period, the RF energy is varied as the measured voltage is kept constant. The treatment interval can have an automatic time-out after a predetermined interval of less that 360 seconds, 240 seconds, 180 seconds, 120 seconds or 90 seconds, as examples.

By using the initial delivery of RF energy through the dielectric structure 150 and contacted tissue in the first, initial constant power mode, a voltage level is recorded (e.g., in the example, at one second) that directly relates to a combination of (i) the surface area of the dielectric structure, and the degree to which wall portions of the dielectric structure have been elastically stretched; (ii) the flow rate of neutral gas through the dielectric structure and (iii) the impedance of the contacted tissue. By then selecting a constant voltage for the second, constant voltage mode that is directly related to the recorded voltage from the first time interval, the length of the second, treatment interval can be the same for all different dimension uterine cavities and will result in substantially the same ablation depth, since the constant voltage maintained during the second interval will result in power that drifts off to lower levels toward the end of the treatment interval as tissue impedance increases. As described above, the controller 130A also can use an impedance level or a selected increase in impedance to terminate the treatment interval.

The algorithm above provides a recorded voltage at set time point in the first mode of RF energy application, but another embodiment can utilize a recorded voltage parameter that can be an average voltage over a measuring interval or the like. Also, the constant voltage in the second mode of RF energy application can include any ramp-up or ramp-down in voltage based on the recorded voltage parameter.

In general, an electrosurgical method for endometrial ablation comprises positioning a RF ablation device in contact with endometrial tissue, applying radiofrequency energy in a first mode based on a predetermined constant power over a first interval, and applying radiofrequency energy in a second mode over a second interval to ablate endometrial tissue, the energy level of the second mode being based on treatment voltage parameters obtained or measured during the first interval. Power during the first interval is constant, and during the second period is varied to maintain voltage at a constant level. Another step in applying RF energy in the first mode includes the step of recording a voltage parameter in the first interval, wherein the voltage parameter is at least one of voltage at a point in time, average voltage over a time interval, and a change or rate of change of voltage. The second mode includes setting the treatment voltage parameters in relation to the voltage parameter recorded in the first interval.

Referring to FIG. 11, it can be understood that an electrosurgical system for endometrial ablation comprises a radiofrequency ablation device coupled to an radiofrequency power supply, and control means connected to the radiofrequency power supply for switching the application of radiofrequency energy between a constant power mode and a constant voltage mode. The control means includes an algorithm that (i) applies radiofrequency energy in the first mode (ii) records the voltage within a predetermined interval of the first mode, and (iii) applies radiofrequency energy in the second mode with constant voltage related to the recorded voltage.

In another aspect, the invention comprises a radiofrequency power supply, a means for coupling the radiofrequency power supply to an ablation device configured for positioning in a uterine cavity, the ablation device comprising a dielectric for contacting endometrial tissue, a system for recording an electrical parameter of the ablation device and contacted tissue, and a feedback system for varying the application of radiofrequency energy to tissue between a constant power mode and a constant voltage mode based on a recorded electrical parameter.

Figure 12:
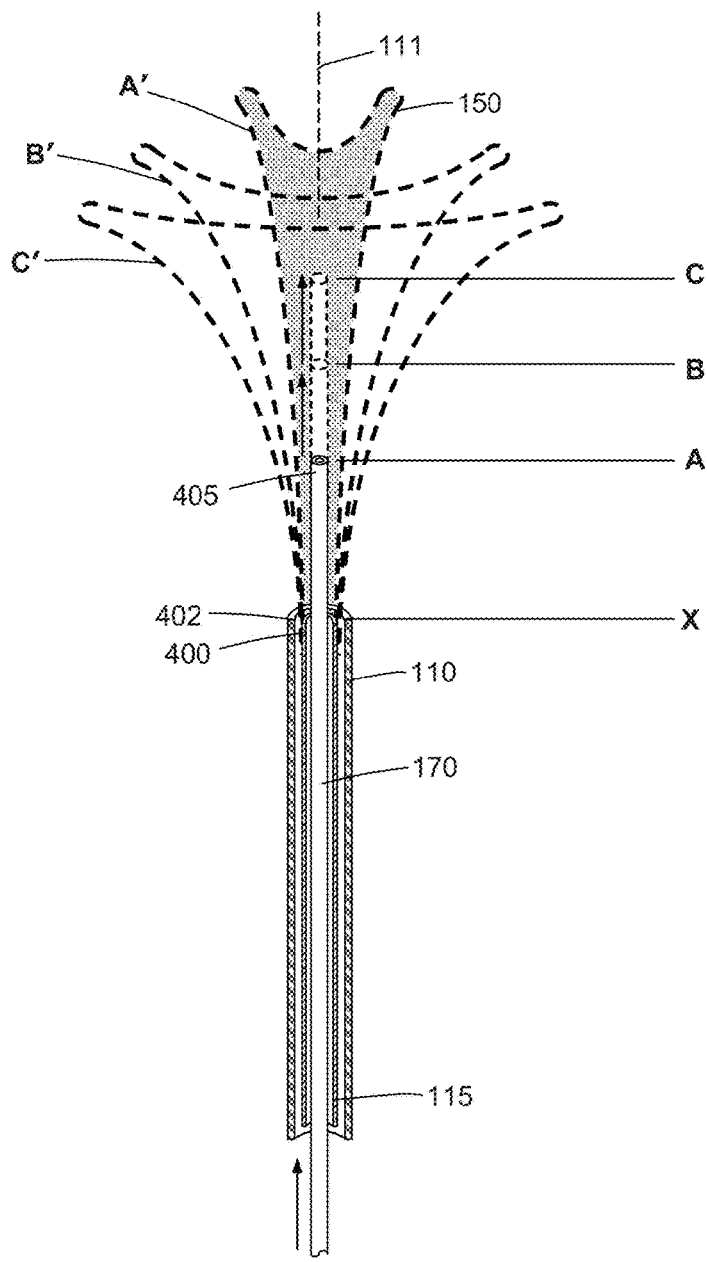
FIG. 12 is a schematic view of the working end of the ablation device of FIGS. 1-2 depicting three outlines of the expandable working end in a range of slightly-expanded to fully-expanded positions.
Figure 13A:
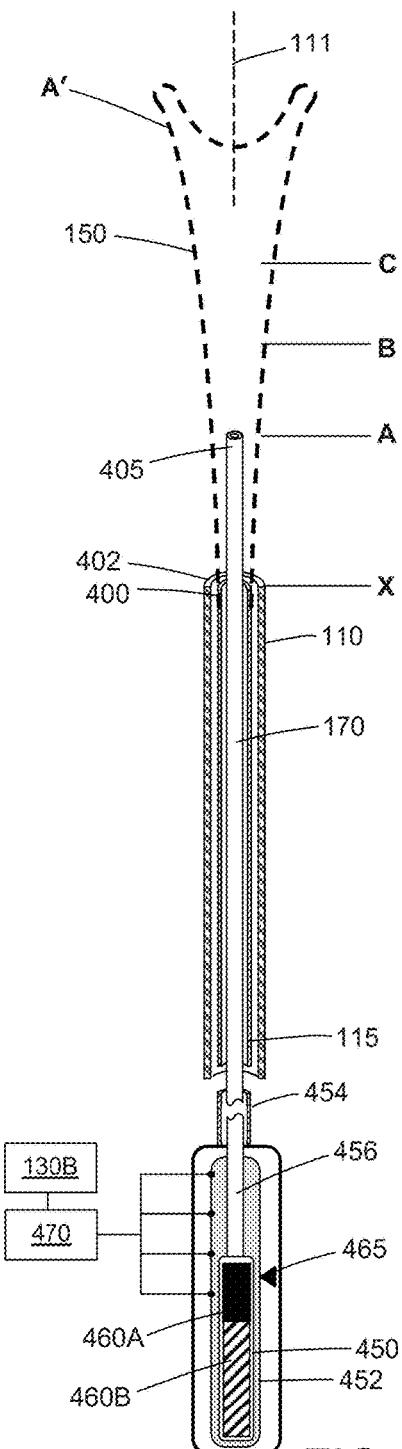
FIG. 13A is a schematic representation of an indicator mechanism in the handle of the ablation device of FIGS. 1-2 for indicating a first degree of expansion of the dielectric structure in a range shown in FIG. 12.
Figure 13B:
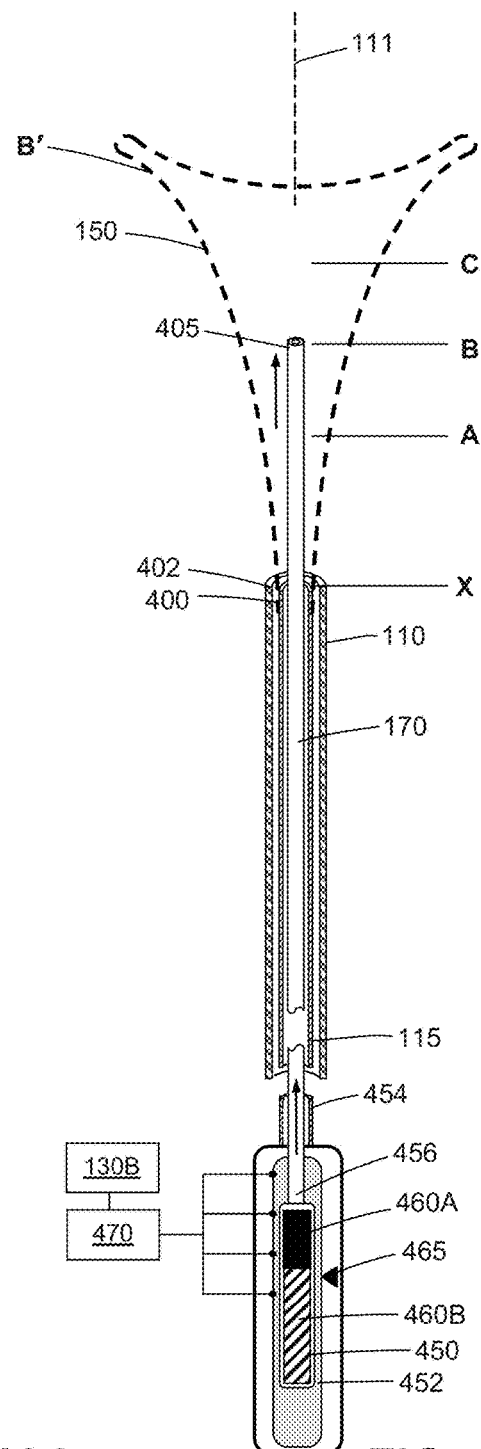
FIG. 13B is a schematic representation of the indicator mechanism of FIG. 13A indicating a second the degree of expansion of the dielectric structure.

In another embodiment of the invention, FIGS. 12, 13A and 13B depict components of the ablation device of FIGS. 1-2 that provide the physician with an indication of the degree to which the dielectric structure 150 has opened in the patient's uterine cavity 302. It can be understood from FIGS. 5, 6 and 8C that the spring frame 155 that moves the dielectric structure 150 from a contracted, linear shape (FIG. 8B) to an expanded, triangular shape (FIG. 8C) results from actuating the handle 106 to move the assembly of inner sleeve 170, intermediate sleeve 115, frame 155 and dielectric structure 150 distally relative to the introducer sleeve 110 to thus expose and deploy the dielectric structure 150 in the uterine cavity 302.

Referring to FIG. 12, it can be seen that inner sleeve 170 and intermediate sleeve 115 are shown for convenience without their respective welded connections to spring frame elements 158a, 158b, 160a and 160b. The frame elements 158a, 158b, 160a and 160b and their springing function can be seen in FIGS. 5 and 6. In FIG. 12, the introducer sheath 110 is shown as being moved proximally relative to the dielectric structure 150 which corresponds to a position of the dielectric structure 150 shown in FIG. 8B. In the schematic view of FIG. 12, the distal end 400 of sleeve 170 has an axial position X and can be approximately the same axial position as the distal end 402 of the introducer sleeve 110. It can be understood that when the dielectric structure 150 and interior spring frame 155 are deployed in a uterine cavity, the spring force of frame 155 will tend to open the dielectric structure 150 from a position in FIG. 8B toward the position of FIG. 8C. In FIG. 12, an initial position of the distal end 405 of sleeve 170 has an axial position indicated at A which corresponds to plan shape A' of the dielectric structure 150. In a typical procedure, the spring force of frame 155 will move the distal end 405 of sleeve 170 toward an axial position B which corresponds to expanded dielectric plan shape B' or toward an axial position C and corresponding expanded dielectric plan shape C'. Dielectric plan C' represents a fully expanded dielectric structure 150. In order to allow the spring force of frame 155 to expand the frame and dielectric structure 150, the physician may gently and very slightly rotate, tilt and translate the expanding dielectric structure 150 in the uterine cavity 302. After thus deploying the dielectric structure, the different dimensions of uterine cavities will impinge on the degree of expansion of the dielectric structure 150—and the size and surface area of the dielectric structure, as an example, will be within the dimension range between plan shapes A' and plan shape C' of FIG. 12.

In one aspect of the invention, it is important for the system and physician to understand the degree to which the dielectric structure 150 and frame 155 has expanded in the uterine cavity. If the dielectric structure 155 has not expanded to a significant degree, it may indicate that the uterine cavity is very small or very narrow, that fibroids are impinging on dielectric structure preventing its expansion, that the uterine cavity is very asymmetric, or that a tip of the dielectric structure and frame 155 has penetrated into an endometrial layer, perforated the uterine wall or followed a dissection path created by a sounding procedure just prior to deployment of the dielectric structure. Further, in one system embodiment, the dielectric structure 150 is preferred to have a minimum surface area directly related to its expanded shape to thus cooperate with an RF energy delivery algorithm.

In one embodiment, the system provides a "degree of frame-open" signaling mechanism for signaling the physician that the frame 155 and dielectric structure 150 has expanded to a minimum predetermined configuration. The signaling mechanism is based on the relative axial location of inner sleeve 170 and sleeve 115 as can be understood from FIGS. 12 and 13A-13B. In FIGS. 1 and 2, it can be seen that a sliding element 450 is exposed in a top portion of handle component 114B to slide axially in a slot 452. In a schematic view of handle component 114b in FIGS. 13A-13B, it can be seen that the proximal end 454 of sleeve 115 is fixed in handle component 114b. Further, the proximal end of 456 of the inner sleeve 170 is connected to the sliding element 450 that slides in slot 452. Thus, it can be understood that inner sleeve 170 is slidable and free-floating in the bore 175 of sleeve 115 and can be moved axially to and fro depending to the opening spring force of frame 155—which force can be constrained by the frame being withdrawn into the bore 120 of introducer sleeve 110 or by uterine walls impinging on the dielectric structure 150 and frame 155 when deployed in a uterine cavity. As can be seen in FIGS. 1, 2, 13A and 13B, the sliding element has at least two axially-extending indicators 460A and 460B that can be different colors that slide axially relative to status-indicating arrow element 465 in a fixed location in the handle 114b. In one embodiment, indicator 460A can be red for "stop" and indicator 460B can be "green", for indicating whether to stop proceeding with the procedure, or to go ahead with the ablation procedure. In FIG. 13A, it can be seen that inner sleeve 170 and its distal end 405 are only axially extended at point A which corresponds to dielectric expansion profile A'. The limited expansion of dielectric structure at profile A' is indicated at the slider 450 wherein the arrow 465 points to the red 'stop" indicator 460A which indicates to the physician to stop and not proceed with the ablation procedure due to limited expansion of dielectric structure 150.

FIG. 13B depicts an extension of inner sleeve 170 and its distal end 405 to axially extended at point B which corresponds to dielectric expansion profile B'. This intermediate expansion of dielectric structure 150 at profile B' is indicated to the physician by observing slider 450 wherein arrow 465 points to the green indicator 460B which indicates "go"—that is, the physician can proceed with the ablation procedure since the dielectric structure 150 and frame 155 have expanded to a predetermined degree that cooperates with an RF energy delivery algorithm. It can be understood from FIG. 13B that sleeve 170 can move axially toward extended position C with corresponding dielectric structure profile C' and indicator arrow 465 will again point to the "go" portion 460B of sliding element which is green.

In another aspect of the invention also depicted in FIGS. 13A-13B, the handle component 114b can include a electrical contact sensor 470 that detects the axial movement of sliding element 450 and sleeve 170 relative to sleeve 115 to thereby provide an electronic signal indicating the degree of expansion of the frame 155 and dielectric structure 150. In one embodiment, the electronic signal communicates with RF controller 130B to disable the system if the relative axial positions of sleeves 170 and 115 do not indicate a predetermined degree of expansion of the frame 155 and dielectric structure. The system can further include an override mechanism, whereby the physician can manipulate the instrument slightly back and forth and rotationally to evaluate whether the frame 155 opens incrementally more. In another embodiment, the electrical sensor 470 can detect a plurality of degrees of expansion of the frame 155 and dielectric structure 150, for example as depicted by an electrical contact be activated at positions AA, BB, CC, and DD of the slider 450 in FIGS. 13A-13B, wherein each degree of expansion of frame 155 signals the controller to select a different RF delivery algorithm. The various different RF delivery algorithms can alter at least one of: (i) the duration of a treatment interval, for example from between 60 seconds and 240 seconds, (ii) the relation between a recorded voltage and a treatment voltage as described in the text accompanying FIG. 11 above (e.g., the treatment voltage can equal the recorded voltage, or vary as a factor about 0.8, 0.9, 1.0, 1.1 or 1.2 times the recorded voltage; (iv) can vary a ramp-up or ramp-down in voltage, or can a time interval of the first and second modes of RF energy delivery described above. The number of degrees of expansion of frame 155 and dielectric structure can range from 1 to 10 or more.

The embodiment of FIGS. 1, 2, 13A and 13B depict indicator subsystems that include visual and electrical signals, but it should be appreciated that the indicator subsystem can provide any single or combination signals that can be visual, aural or tactile with respect to the operator and/or electrically communicate with microprocessors, programmable logic devices or controllers of the ablation system.

FIGS. 14A-14B depict another device corresponding to the invention, which comprises a seal assembly 500 that is configured for positioning in a patient's endocervical canal. FIG. 14A shows the cervical seal assembly 500 in a first non-expanded configuration which includes an elongated sleeve 505 that extends along longitudinal axis 508 with a tool-receiving passageway 510 extending from proximal end 512a to distal end 512b of the sleeve 505. The sleeve can have an outer diameter ranging from about 5 mm to 8 mm. The elongated sleeve 505 carries an expandable, inflatable balloon 515 with a first or distal balloon portion 516 that expands to a radial dimension of up to 20 mm. A second balloon portion 518 comprises an annular thin wall formed with a plurality of annular or helical ridges or undulations 522 spaced apart by annular recessed region(s) indicated at 524. The annular ridges 522 can have any suitable dimension and can be continuous or spaced-apart. The radial height of the ridges above the recesses 524 can range from about 1 to 5 mm. The balloon 515 can be fabricated of a biocompatible elastomeric material such as silicone. The balloon wall can have reinforcing braids or other woven material therein, or can have metal spring wire material embedded therein to form the ridges 522 and annular recesses. An inflation source 525 couples to inflation port 526 to expand both the first portion 516 and second portion 518 of the balloon 515. The inflation source 525 can comprise a syringe and the inflation media can comprise a gas or a liquid. In another embodiment, the seal and inflation source can be configured to inflate the first and second balloon portions, 516 and 518, independently with each balloon portion having an independent inflatable chamber.

Figure 15A:
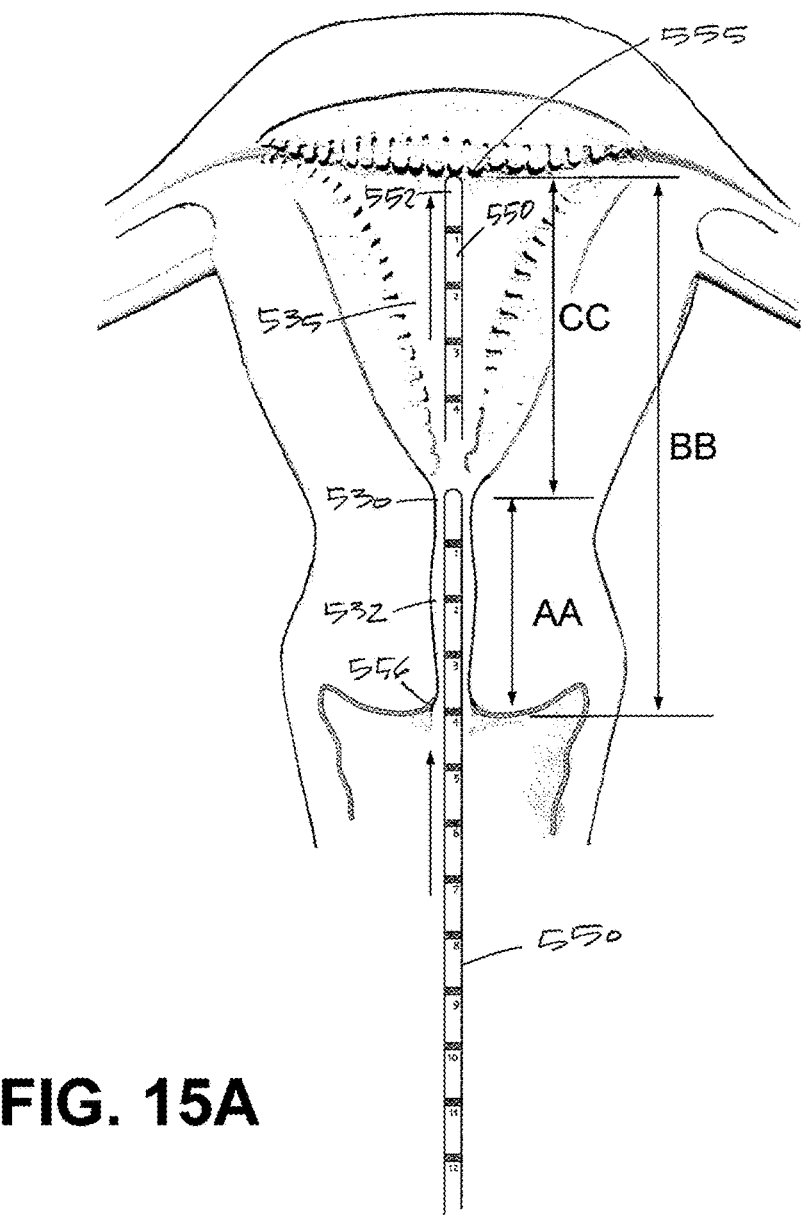
FIG. 15A is a schematic view showing multiple steps of using a sound to determine the length of an endocervical canal and the length of the uterine cavity.

The seal assembly 500 of FIGS. 14A-14B has an overall length that is adapted to seal the longest potential lengths of a patient's endocervical canal defined as and by the distance between the internal and external cervical ostia, as measured or estimated by the user, and can be, for example, about 1 cm to 8 cm. The seal assembly 500 is designed to position the distal balloon portion 516 in and at the level of the internal cervical os, or immediately above the internal cervical os, or at the level of the lower uterine segment 530 (per user choice) following measurement of the length of the endocervical canal 532 and uterine cavity 535 using methods described below (FIG. 15A). For this reason, the seal assembly 500 carries at least one set of marks 540 or indicators that indicate the length of the seal extending proximally from a proximal end or face of the distal balloon portion 516. In FIGS. 14A-14B, it can seen that the markings can consist of (i) numbers indicating the centimeters from the distal balloon 516 and/or (ii) colored markings 540 on the balloon ridges 522 or elsewhere on the balloon. In use, the physician then will insert/advance the seal assembly 500 into the endocervical canal 532 to the measured length of the canal, and then expand the first and second balloon portions to seal the canal, as will be described further below. The seal assembly 500 also can have a marking, such as a color marker 545 at the proximal end 512a of the sleeve 505, to register against marking on the shaft 560 of an ablation device, as will be described in detail below.

Now turning to FIG. 15A, a method of measuring the lengths of an endocervical canal 532 and a uterine cavity 535 is shown. FIG. 15A shows schematically a probe (uterine dilator or uterine sound) 550 being inserted through the endocervical canal 532 until the tip 552 of the probe reaches a point of resistance commonly associated with the anatomical location of the internal cervical os 530. The typical length of the endocervical canal 532 is indicated at AA and can range from about 1 cm to 8 cm. After taking note of the distance assessed, the physician advances the probe until its distal tip 552 contacts the fundus 555 of the uterus (as shown in the upper half of FIG. 15A). The combined axial length BB of the endocervical canal 532 and the uterine cavity 535 then can be determined by the markings on the sound 550 in relation to the external os 556. By this means, the physician can determine the uterine cavity length CC by subtracting the canal length AA from the combined axial length BB. For example, in FIG. 15A, the endocervical canal has a length AA of 4 cm and the uterine cavity 535 has a length CC of about 5.5 cm as determined by subtracting length AA from length BB.

Figure 15B:
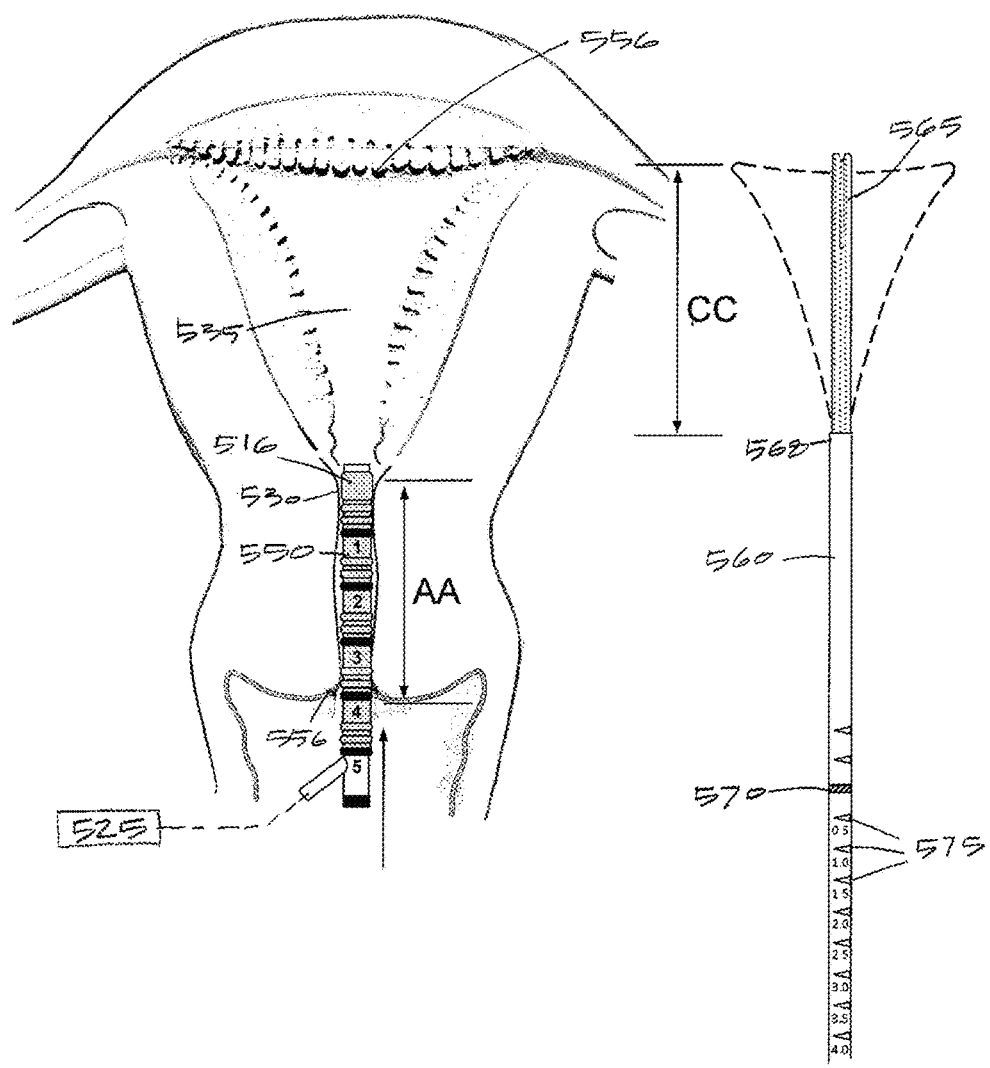
FIG. 15B is a schematic view showing the steps of (i) inserting the seal assembly of FIG. 14A in a non-expanded position into the endocervical canal and (ii) adjusting the length of the ablation device of FIG. 8A to FIG. 9 to correspond to the calculated length of the uterine cavity.
Figure 15C:
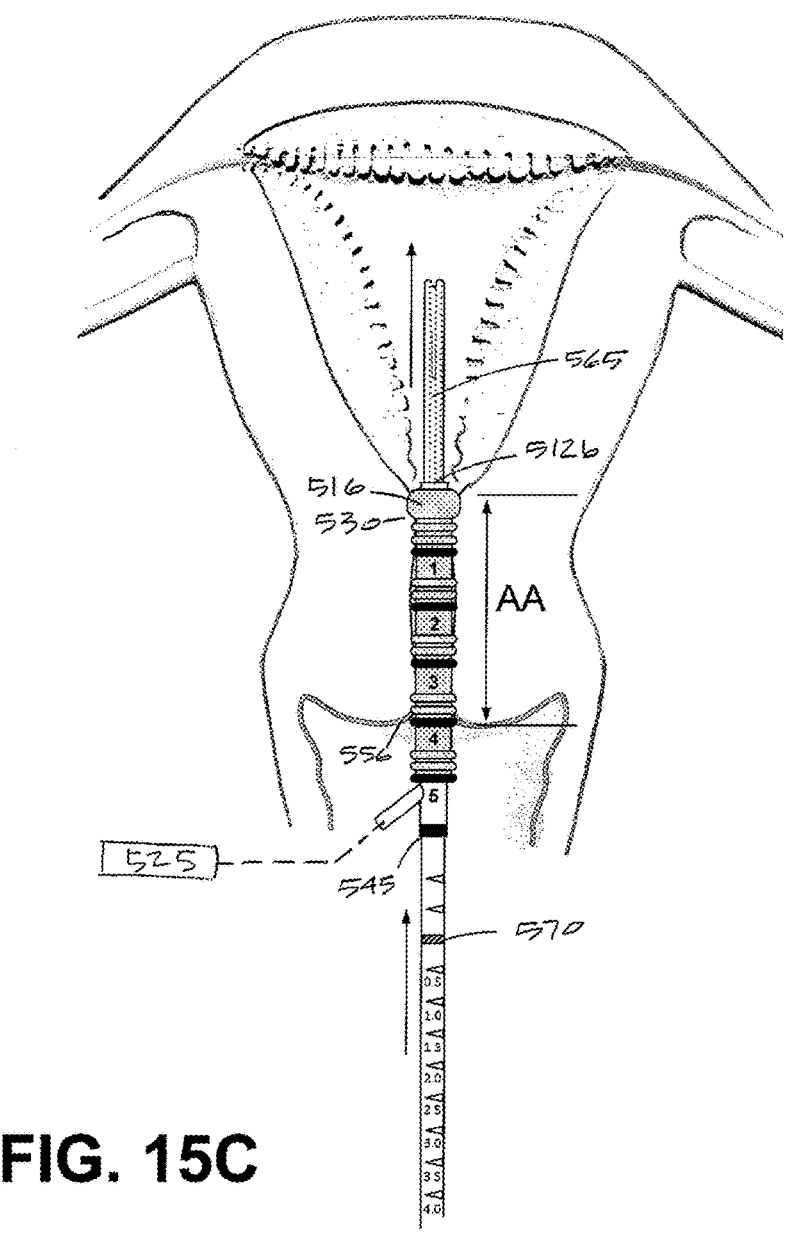
FIG. 15C shows the steps of (i) inflating the seal assembly to an expanded position in the endocervical canal and (ii) introducing the ablation device of FIG. 8A to FIG. 9 into the uterine cavity.

FIG. 15B illustrates a subsequent step of inserting/advancing the seal assembly 500 of FIG. 14A in a non-expanded position into the endocervical canal 532 such that distal balloon portion 516 is at the previously determined and calculated level of the internal os 530, using the markings 540 on the seal assembly 500. Thereafter, the balloon portions 516 and 518 of the seal are inflated and radially expanded as shown in FIG. 15C.

In another step of the method, FIG. 15B shows the ablation device shaft 560 and expandable dielectric 565 being prepared for use. More particularly, the axial length of the dielectric 565 is adjusted to match the axial length CC of the uterine cavity. In FIG. 15B, it can be seen that the shaft 560 of the ablation device carries markings to insure the dielectric 565 is properly positioned relative to the seal assembly 500 and the uterine cavity 535. In one embodiment, the markings include a marker 566 spaced proximally from the distal end 568 of the shaft 560 that corresponds to the axial length of the seal assembly 500. Using the seal assembly 500 and the ablation device, the physician can assume proper placement when the marker 570 on shaft 560 is adjacent the marker 545 on the seal assembly 500. FIG. 15C illustrates the step of inflating the seal assembly 500 to an expanded position in the endocervical canal and introducing the shaft 560 and dielectric 565 of ablation device through the seal assembly 500 into the uterine cavity 535.

Figure 15D:
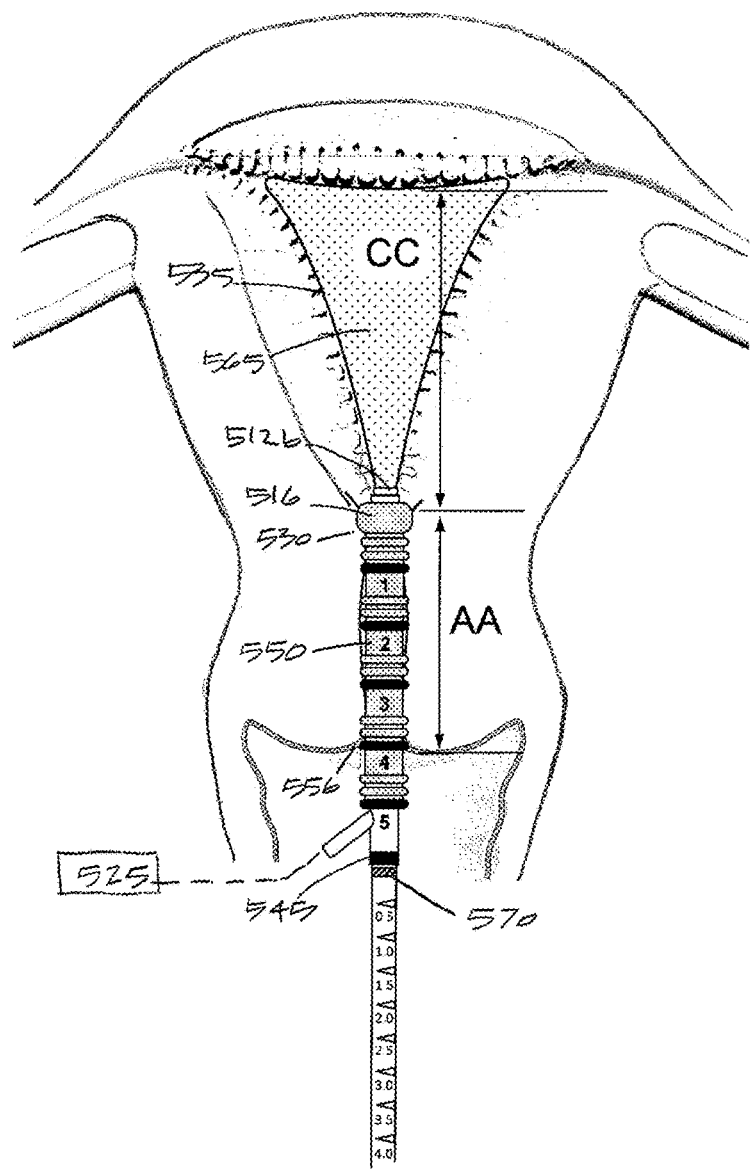
FIG. 15D shows the steps of (i) expanding the working end dielectric in the uterine cavity, and (ii) observing the markings on the introducer shaft with reference to the seal assembly to insure that previous measurements of length of the uterine cavity matches with the deployed position of the working end.

FIG. 15D next shows the step of expanding the dielectric 565 in the uterine cavity 535, and observing the marking 570 on the introducer shaft 560 with reference to the seal assembly 500 to insure that previous measurements of length of the uterine cavity matches with the deployed position of the dielectric 565. In FIG. 15D, it can be seen that markers 570 and 545 are adjacent to one another which depicts a proper deployment. In this configuration, the base of the triangulation of the dielectric 565 will be disposed proximate the distal end 512b of the seal assembly 500 and proximate the internal os 530 of the uterine cavity as shown in FIG. 15D.

Figure 16:
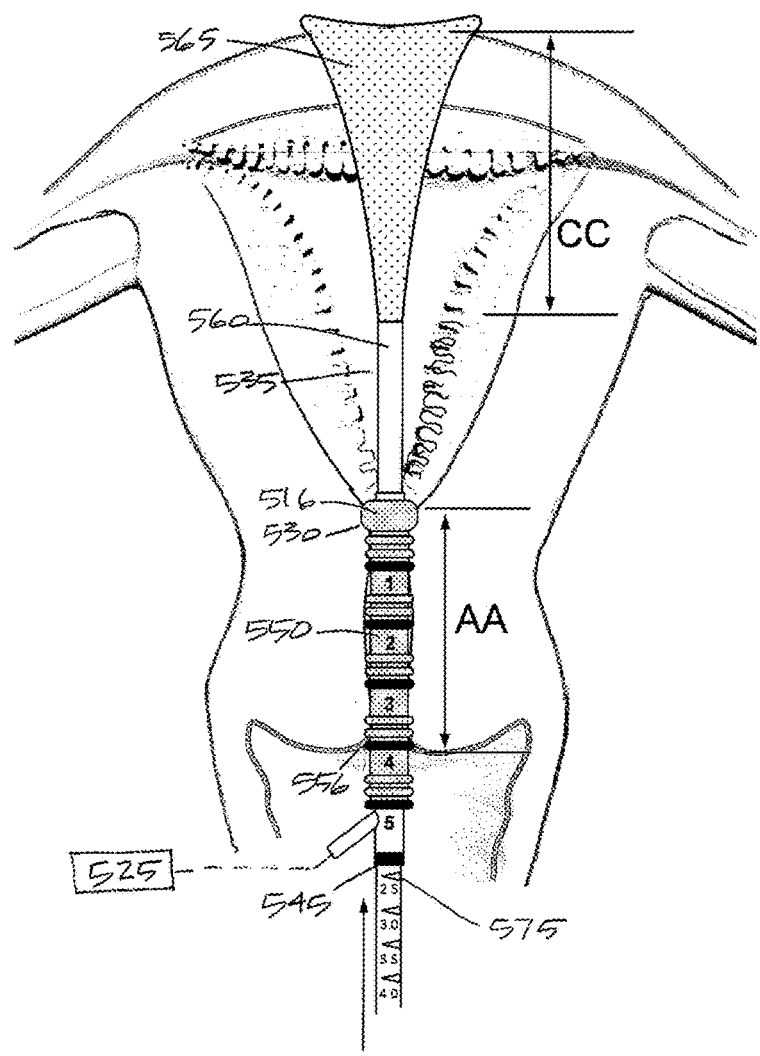
FIG. 16 shows an exemplary situation in which the markings on the introducer shaft relative to the seal assembly indicates improper positioning of the working end.

FIG. 16 depicts a situation in which the markers on the seal assembly 500 and shaft 560 of the ablation device can indicate an improper deployment of the dielectric 565 or the seal assembly 500. In FIG. 16, it can be seen that seal assembly 500 is in its proper position but that the dielectric 565 has been extended through a perforation in the fundus of the uterus and partially expanded. This condition is easily recognized by the physician observing that markings 575 on shaft 560 of the ablation device indicate the dielectric had been extended about 2.5 cm distally beyond it proper relationship with the seal assembly 500. In such a situation, the physician would know to start the procedure over to determine what error has been made. The error may relate to miscalculation of the length of the endocervical canal or uterine cavity, a misplacement of the seal assembly or misplacement of the dielectric working end 565.

In another embodiment, the instrument shaft 560 and/or the seal assembly 500 can carry cooperating electrical sensors that determine whether the shaft 560 and seal 500 are in a proper axial relationship to proceed with an ablation procedure. The sensors can be coupled to the controller to prevent the delivery of ablation energy unless the shaft 560 and seal 500 are in the proper axial relationship or the sensors can actuate a signal, such as a tone, light signal or tactile signal.

In another embodiment, the instrument shaft comprises and outer sleeve and an inner sleeve that carries the dielectric structure as depicted in FIGS. 5-7 and FIGS. 12-13B. The relative axial position of the outer and inert sleeves, for example sleeves 110 and 115 in FIG. 12, determines the axial length of the dielectric structure 150 in FIG. 12. Such an embodiment can include electrical position sensors for determining the axial relationship between the sleeves and thus provide signals as to the axial length of the dielectric structure. This signal can be provided to the controller to provide a visual or other display of the axial length of the dielectric structure. This embodiment can be combined with the previously described embodiment in which position sensors provide a signal relating to axial relationship of the outer sleeve (i.e., shaft 560) and the seal assembly 500 of FIGS. 14A-14B. An embodiment with such position sensors can then be coupled to the controller which can carry software that can use the relative axial positions of the three sleeves to determine that (i) system deployment is proper or (ii) to alert the physician that some aspect of system deployment is improper. Such a system can further include a lock-out mechanism to prevent RF energy from being applied through the ablation device if the system deployment is improper. In general, a device corresponding to the invention comprises first, second and third sleeves extending about an axis, and a plurality of position sensors for determining the axial relationship between the three sleeves to determine proper deployment of an ablation system relative to a patient's endocervical canal and uterine cavity.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method of using an endometrial ablation system, comprising
positioning a seal assembly in an endocervical canal with a distal seal end proximate an internal os;
introducing a probe shaft through a central passage in the seal assembly into a uterine cavity;
expanding a distal expandable-collapsible energy-delivery surface carried by the probe shaft so that the expanded surface contacts a wall of the uterine cavity;

observing the axial relationship between the seal assembly and probe shaft to check system parameters against measurements of the endocervical canal and uterine cavity; and delivering energy through the energy-delivery surface into the wall of the uterine cavity.

2. The method of claim 1 wherein positioning the seal assembly is preceded by measuring a length of the endocervical canal.

3. The method of claim 1 wherein positioning the seal assembly is preceded by measuring a length of the uterine cavity.

4. The method of claim 1 wherein positioning the seal assembly includes expanding a cross-section of the seal assembly.

5. The method of claim 1 wherein introducing the probe shaft through the central passage in the seal assembly is preceded by setting a length dimension of the energy-delivery surface when expanded in the uterine cavity.

\* \* \* \* \*